US012193815B2

(12) United States Patent
Jia et al.

(10) Patent No.: US 12,193,815 B2
(45) Date of Patent: Jan. 14, 2025

(54) SYSTEMS AND METHODS FOR CAPILLARY OXIMETRY USING OPTICAL COHERENCE TOMOGRAPHY

(71) Applicant: Oregon Health & Science University, Portland, OR (US)

(72) Inventors: Yali Jia, Portland, OR (US); Shaohua Pi, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 1049 days.

(21) Appl. No.: 16/991,806

(22) Filed: Aug. 12, 2020

(65) Prior Publication Data

US 2021/0045672 A1    Feb. 18, 2021

Related U.S. Application Data

(60) Provisional application No. 62/885,734, filed on Aug. 12, 2019.

(51) Int. Cl.
*A61B 5/1455*    (2006.01)
*A61B 3/00*    (2006.01)
(Continued)

(52) U.S. Cl.
CPC ........ *A61B 5/14555* (2013.01); *A61B 3/0025* (2013.01); *A61B 3/102* (2013.01);
(Continued)

(58) Field of Classification Search
CPC ... A61B 5/14555; A61B 3/0025; A61B 3/102; A61B 3/1233; A61B 5/14546;
(Continued)

(56) References Cited

U.S. PATENT DOCUMENTS

2016/0284085 A1*    9/2016    Huang ................ G06T 7/136

OTHER PUBLICATIONS

NPL Liu (Liu, Rongrong, et al. "Single capillary oximetry and tissue ultrastructural sensing by dual-band dual-scan inverse spectroscopic optical coherence tomography." Light: Science & Applications 7.1 (2018): 57.) (Year: 2018).*

(Continued)

*Primary Examiner* — Eric J Messersmith
*Assistant Examiner* — Chanel J Jhin
(74) *Attorney, Agent, or Firm* — Schwabe, Williamson & Wyatt, P.C.

(57) ABSTRACT

Disclosed herein are methods and systems for capillary oximetry (e.g., retinal capillary oximetry) using optical coherence tomography (OCT). The method may include obtaining an OCT angiography dataset, performing capillary segmentation based on the OCT angiography dataset to obtain capillary segments, resampling, registering, and/or averaging B-scans of the OCT angiography dataset that correspond to a first capillary segment of the capillary segments to obtain an averaged B-scan for the first capillary segment, determining an anterior and posterior border of the first capillary segment, and determining an oxygen saturation of the first capillary segment based on the averaged B-scan, the anterior border, and the posterior border. Other embodiments may be described and claimed.

19 Claims, 23 Drawing Sheets

(19 of 23 Drawing Sheet(s) Filed in Color)

(51) Int. Cl.
  *A61B 3/10* (2006.01)
  *A61B 3/12* (2006.01)
  *A61B 5/00* (2006.01)
  *A61B 5/145* (2006.01)
  *G16H 10/40* (2018.01)
  *G16H 50/30* (2018.01)
  *G16H 50/50* (2018.01)

(52) U.S. Cl.
  CPC ........ *A61B 3/1233* (2013.01); *A61B 5/14546* (2013.01); *A61B 5/7278* (2013.01); *G16H 10/40* (2018.01); *G16H 50/30* (2018.01); *G16H 50/50* (2018.01)

(58) Field of Classification Search
  CPC ...... A61B 5/7278; G16H 50/50; G16H 10/40; G16H 50/30
  USPC .......................................................... 600/320
  See application file for complete search history.

(56) References Cited

OTHER PUBLICATIONS

Bhuiyan, Alauddin, et al. "Automatic detection of vascular bifurcations and crossovers from color retinal fundus images." 2007 Third International IEEE Conference on Signal-Image Technologies and Internet-Based System. IEEE, 2007. (Year: 2007).*

Meng, Xianjing, et al. "A framework for retinal vasculature segmentation based on matched filters." Biomedical engineering online 14 (2015): 1-20. (Year: 2015).*

Villalobos-Castaldi, M., and Edgardo M. Felipe-Riverón. "Fast automatic retinal vessel segmentation and vascular landmarks extraction method for biometric applications." IEEE International Conference on Biometrics, Identity and Security. vol. 54. 2009. (Year: 2009).*

* cited by examiner

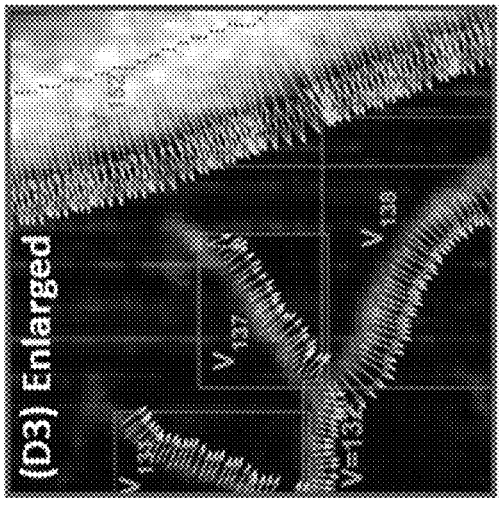
Figure 4A | Figure 4B | Figure 4C
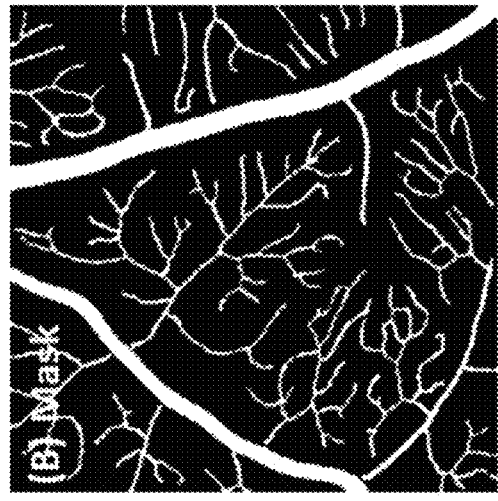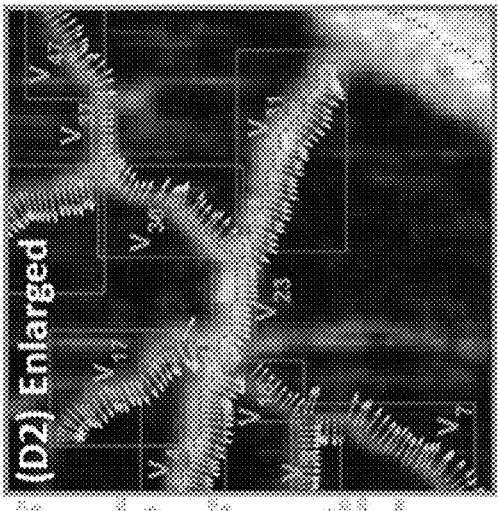
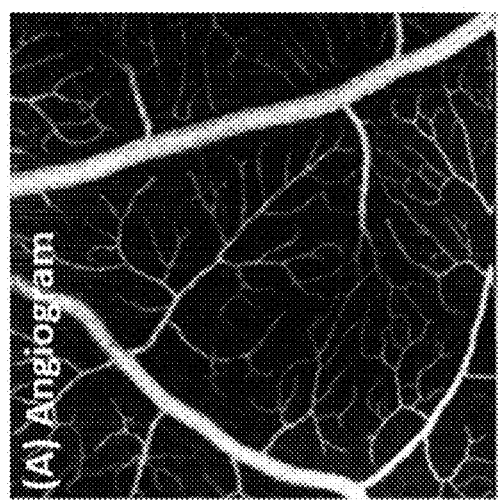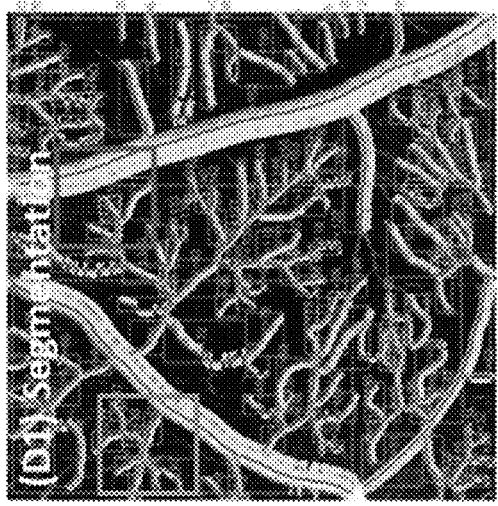
Figure 4D1 | Figure 4D2 | Figure 4D3

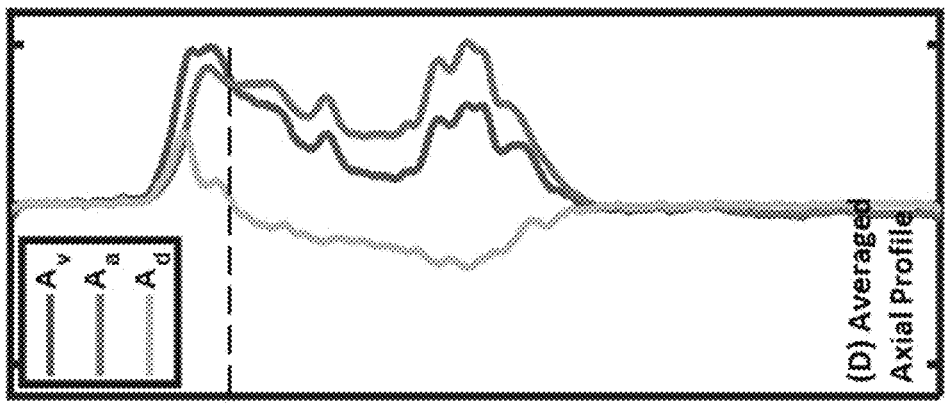
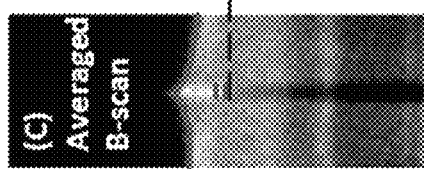
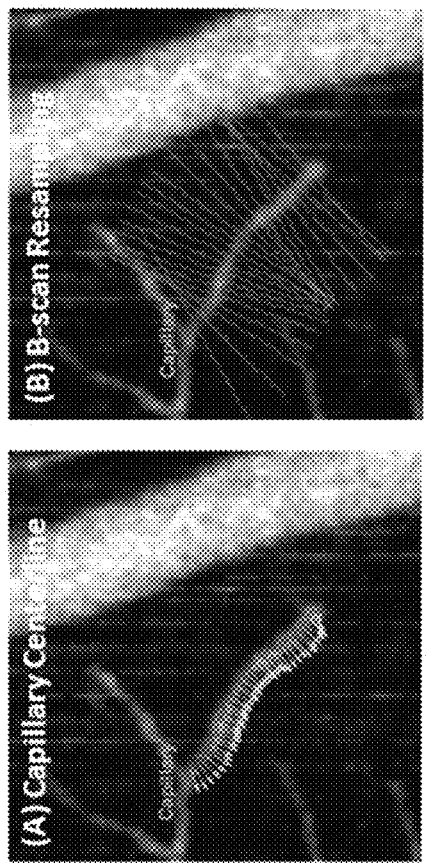
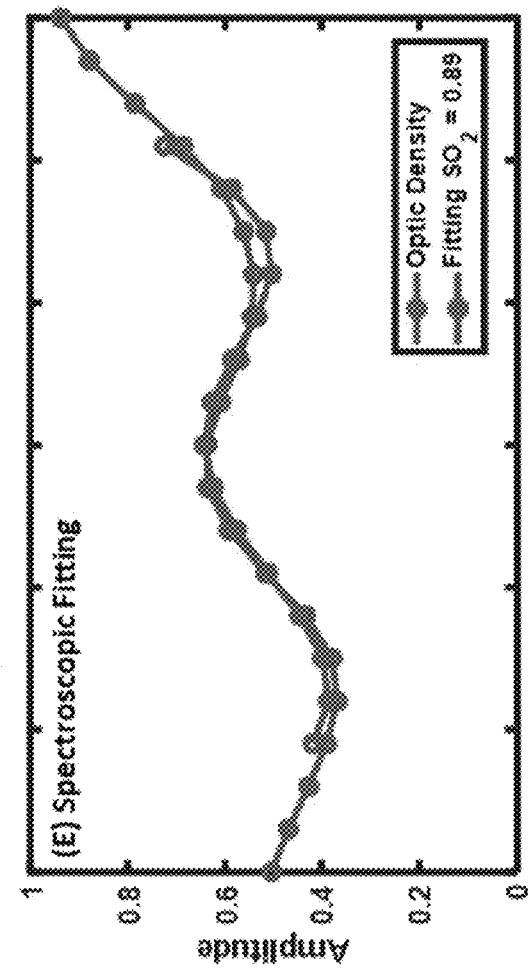
Figure 6A  Figure 6B  Figure 6C  Figure 6D  Figure 6E

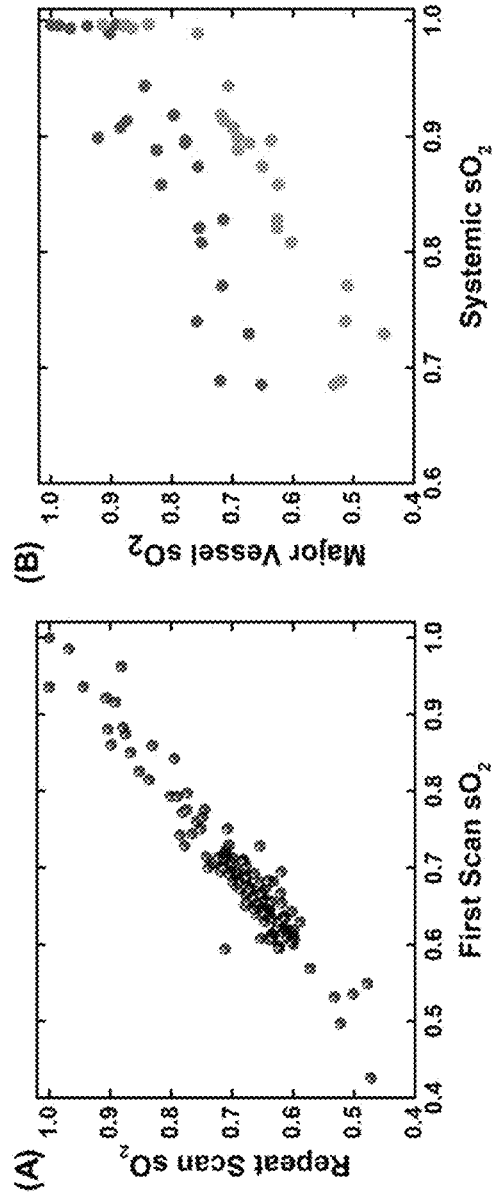
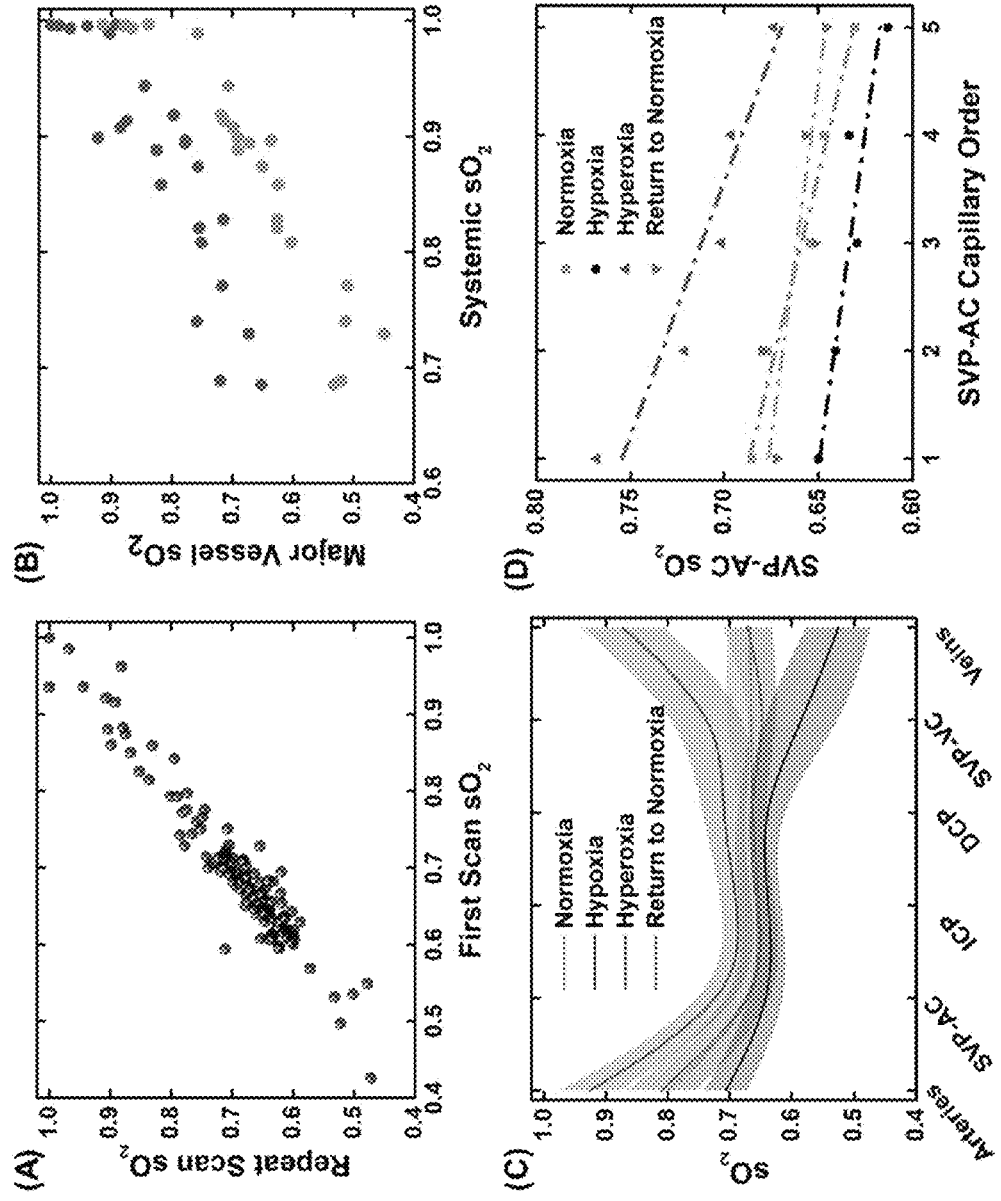
Figure 13A
Figure 13B
Figure 13C
Figure 13D

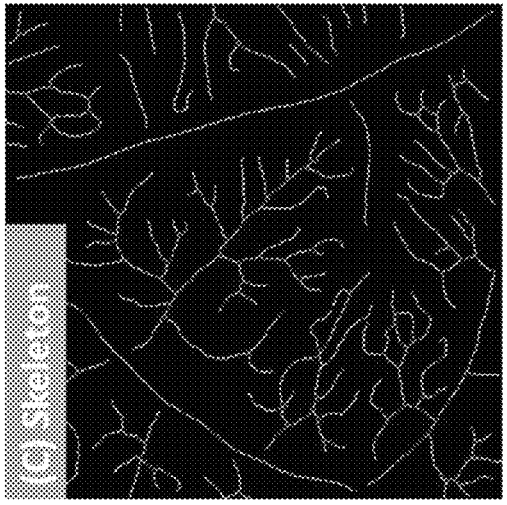
Figure 14C
Figure 14B
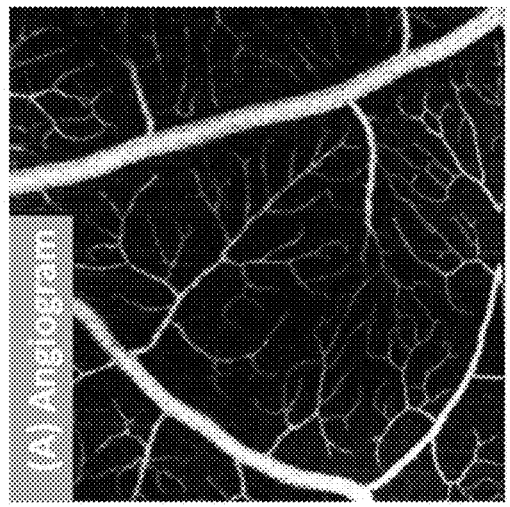
Figure 14A
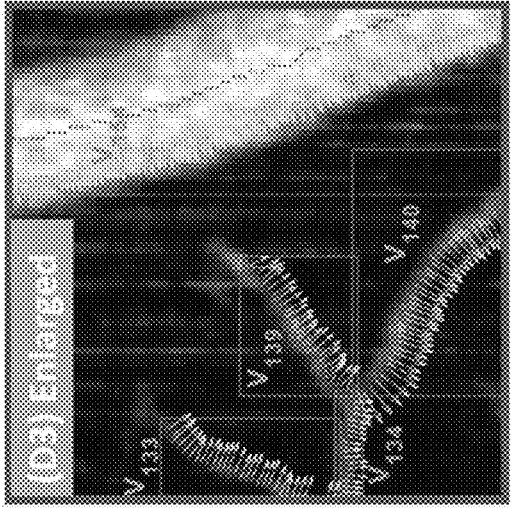
Figure 14D3
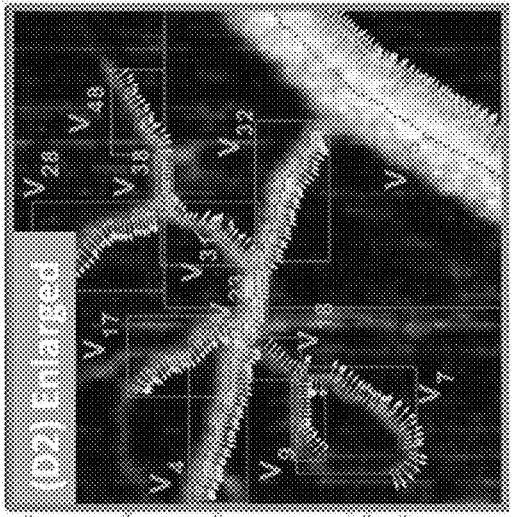
Figure 14D2
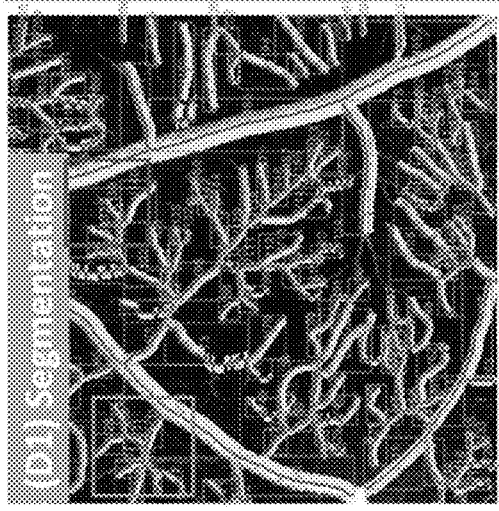
Figure 14D1

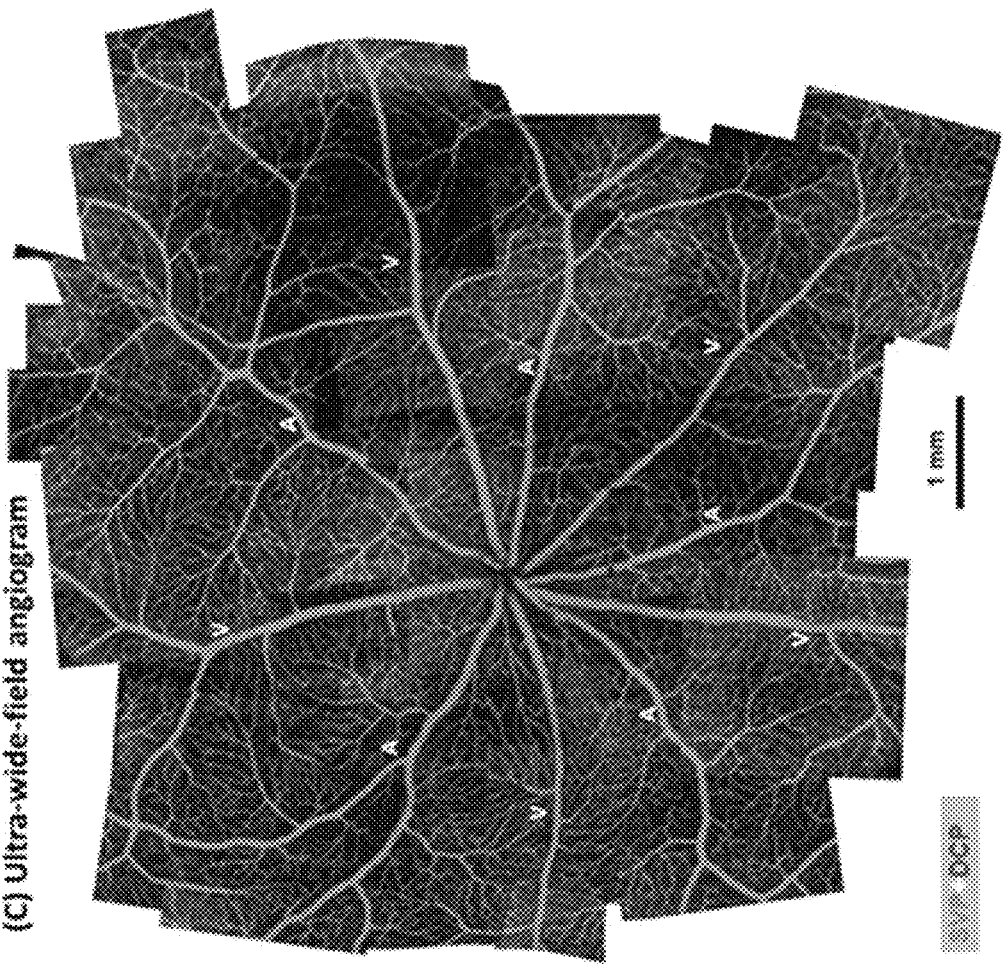
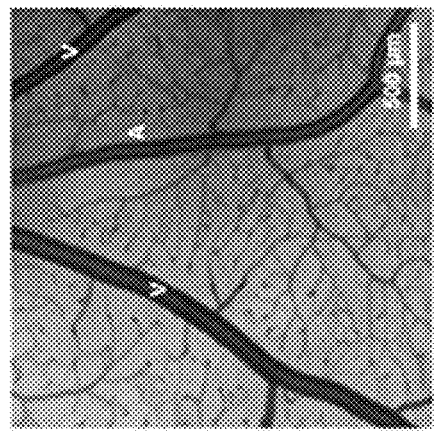
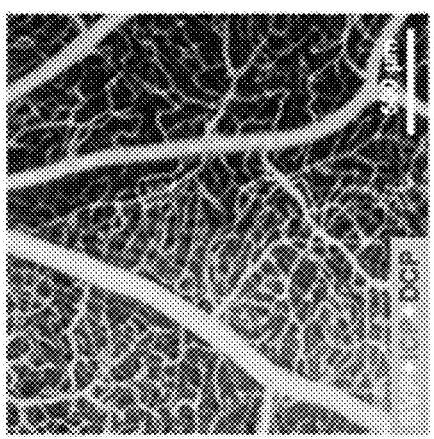
Figure 15A
Figure 15B
Figure 15C

Figure 23A
Figure 23B
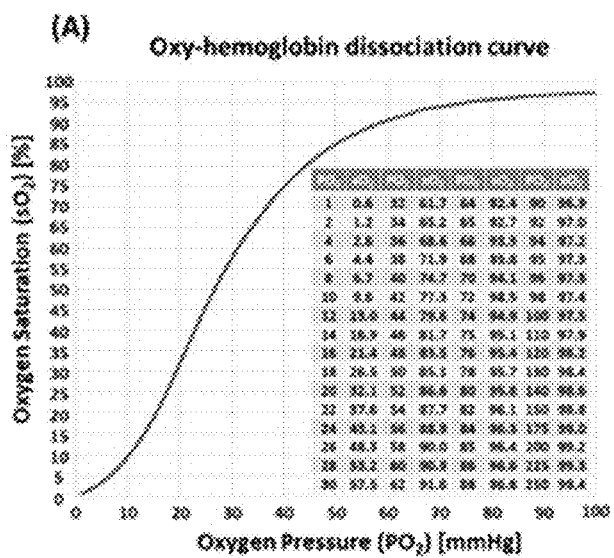
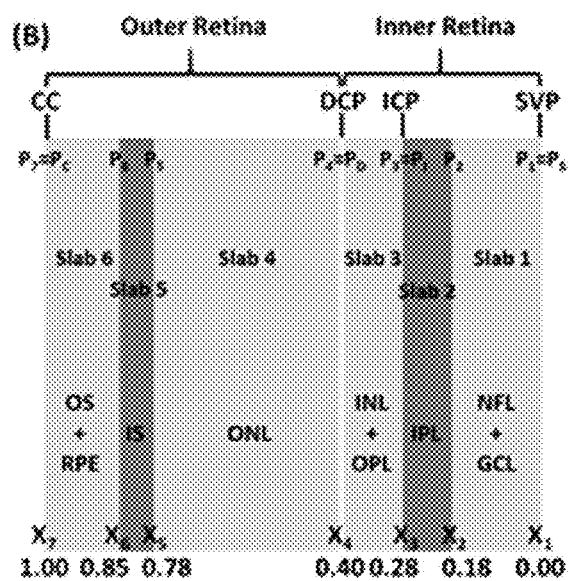
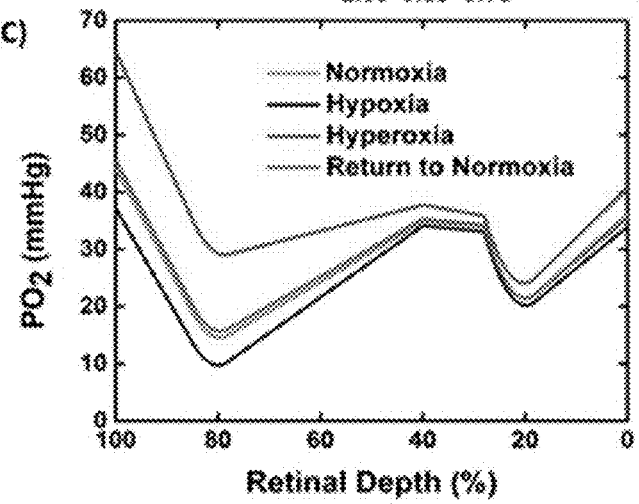
Figure 23C

SYSTEMS AND METHODS FOR CAPILLARY OXIMETRY USING OPTICAL COHERENCE TOMOGRAPHY

CROSS REFERENCE TO RELATED APPLICATION

The present application claims priority to U.S. Provisional Patent Application No. 62/885,734, titled "SYSTEMS AND METHODS FOR CAPILLARY OXIMETRY USING OPTICAL COHERENCE TOMOGRAPHY," filed Aug. 12, 2019, the disclosure of which is hereby incorporated by reference in its entirety.

FIELD

Generally, the field involves methods of imaging using optical coherence tomography. In particular, the field involves methods of capillary oximetry using optical coherence tomography (OCT).

BACKGROUND

Altered oxygen supply is thought to be a critical factor underlying many retinal disorders that may precede loss of visual acuity and observable changes in vascular morphology. Changes in retinal oxygen consumption could affect blood oxygen saturation ($sO_2$), which is the ratio of oxygenated hemoglobin to the total hemoglobin concentration in blood. If quantified accurately, $sO_2$ could be used as a biomarker to monitor retinal metabolism and provide a valuable early indicator of ocular disease.

Measurement of blood oxygen saturation is called oximetry, and relies on the absorption contrast of oxy- and deoxy-hemoglobin. For the assessment of systemic oxygen saturation levels of blood, pulse oximetry is usually applied, in which a probe is placed on a body part, such as a finger or ear lobe. The probe is equipped with a pair of small light-emitting diodes (LEDs) that illuminate the target with two light beams at different wavelengths (usually red and infrared light at $\lambda=660$ and $\lambda=940$ nm, respectively). Absorption of light at these wavelengths differs between bloods at different $sO_2$—more oxygenated hemoglobin absorbs relatively more light in the infrared. Though pulse oximetry is simple and effective in predicting the health of a person with a condition that affects overall $sO_2$ level, the technique has no concept of spatial resolution and lacks the ability to differentiate $sO_2$ levels between arteries and veins.

For ocular and many other diseases, systemic $sO_2$ is usually not affected. Alterations are frequently localized at lesions and the effects differ in arteries and veins. Therefore, when assessing $sO_2$ in ophthalmic vessels, the ability to discriminate results from arteries and veins is highly desirable. For this reason, the possibility of developing retinal oximetry with spatial capability has been explored using fundus photography, scanning laser ophthalmoscopy, and photoacoustic microscopy. These efforts relied on principles similar to pulse oximetry, i.e. calculating $sO_2$ from the optical density ratio between two or more wavelengths. These methods, however, face many problems in practical applications. For example, some techniques have difficulties separating signal from blood from other retinal pigments, some may require direct contact with eyelid, and some may have limited visualization of retinal capillaries because of poor resolution.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIGS. 4A, 4B, and 4C illustrate vascular segmentation in 2-D en face images. FIG. 4A is a projected angiogram showing the vascular plexus in en face image. FIG. 4B illustrates a vascular binary mask. FIG. 4C illustrates a vascular skeleton overlaid with detected bifurcation-points (red dots).

FIG. 4D1 illustrates vascular segmentation results labeled with vascular segment number (green text), region (green box) and normal direction (yellow arrows).

FIG. 4D2 illustrates a detailed view of the region marked by the blue box in FIG. 4D1.

FIG. 4D3 illustrates a detailed view of the region marked by the red box in FIG. 4D1.

FIG. 5A illustrates a volumetric angiogram. FIG. 5B illustrates vascular segmentation results labeled with vascular segment number (green text), region (green box) and normal direction (yellow arrows).

FIGS. 6A, 6B, 6C, 6D, and 6E illustrate oximetry processing on a capillary segment. FIG. 6A illustrates that normal directions (yellow arrows) were extracted along the detected capillary centerline (red). As shown in FIG. 6B, B-scans resampled along the normal directions of the capillary segment (magenta lines). As shown in FIG. 6C, the resampled B-scans were registered and averaged to localize the posterior border (red) of the capillary. FIG. 6D illustrates the averaged capillary reflectance axial profile ($A_c$), and averaged reflectance axial profile of the entire B-scan ($A_a$), as well as their difference ($A_d$). The posterior border (black dash line) is detected by the zero-crossing depth of the difference profile Ad. As shown in FIG. 6E, capillary $sO_2$ was derived by a spectroscopic fitting (red) to the detected spectrum (blue).

FIG. 8 shows=representative capillary $sO_2$ along with that in major vessels (A: artery, V: vein) in one rat retina responding to regulation in oxygen concentration in inhaled gas, from 21% (normoxia) to 15% (hypoxia), then to 100% (hyperoxia) and to 21% (return to normoxia). The angiogram (2×2-mm) was obtained by averaging all 8 scans at all conditions acquired in the same region. The $sO_2$ in capillary segments corresponded to trends shown by the $sO_2$ in major vessels, which decreased with the reduction of oxygen concentration in the inhaled gas.

FIGS. 13A-13D illustrate statistics of changes in vascular $sO_2$ with inhaled oxygen concentration, from normoxia to hypoxia, then to hyperoxia and return to normoxia. FIG. 13A illustrates the relationship between the averaged $sO_2$ in each plexus between the first session and second session indicated good repeatability of capillary oximetry. FIG. 13B illustrates the correlation of major vessel $sO_2$ with changes in systemic arterial $sO_2$, which decreased in hypoxia and increased in hyperoxia, as compared to normoxia. Data point symbol colors indicate arteries (red) and veins (green). FIG. 13C illustrates the mean±standard deviation of $sO_2$ in retinal arteries, SVP arterial capillaries (SVP-AC), ICP capillaries, DCP capillaries, SVP venous capillaries (SVP-VC), and retinal veins for each concentration of inspired oxygen. FIG. 13D illustrates the SVP-AC $sO_2$ decreased with increasing capillary order, indicating oxygen delivery along these capillaries.

FIGS. 14A, 14B, 14C, 14D1, 14D2, and 14D3 illustrate capillary segment extraction. FIG. 14A is an en face angiogram (2×2-mm) showing the superficial vascular plexus. FIG. 14B is a vascular binary mask obtained by thresholding the enhanced angiogram. FIG. 14C is a skeleton showing vascular centerlines. The detected bifurcation and overlay points are marked by red dots. FIG. 14D1 illustrates detected capillary segments in the scanned field of view labeled with vascular segment sequence number (green text), region (green boxes) and normal direction (yellow arrows). FIGS. 14D2 and 14D3 illustrate enlarged, detailed views corresponding to the blue and red boxes in FIG. 14D1, respectively.

FIG. 15A is an en face reflectance image showing inter-plexus capillaries appearing as dark spots. A: artery. V: vein. FIG. 15B illustrates overlaid en face angiograms of the three vascular/capillary plexuses demonstrate the detailed retinal circulatory organization. SVP: superficial vascular plexus. ICP: intermediate capillary plexus. DCP: deep capillary plexus. FIG. 15C illustrates an ultra-wide-field angiogram stitched from multiple scans with smaller field of view.

FIG. 19A is an angiogram volume scan. FIG. 19B shows capillary segmentation. FIG. 19C shows oxygen saturation ($sO_2$).

FIG. 23A illustrates an oxy-hemoglobin dissociation curve that relates oxygen pressure ($PO_2$) with $sO_2$ in the blood. In FIG. 23B, the retina is modeled as six slabs to simulate the axial $PO_2$ profile from $PO_2$ values ($P_S$, $P_I$, $P_D$, and $P_C$) at four capillary plexuses: SVP, ICP, DCP, and choriocapillaris (CC). X: normalized retina depth. NFL: nerve fiber layer, GCL: ganglion cell layer, IPL: inner plexiform layer, INL: inner nuclear layer, OPL: outer plexiform layer, ONL: outer nuclear layer, IS: photoreceptor inner segments, OS: photoreceptor outer segments, RPE: retinal pigment epithelium. FIG. 23C illustrates the calculated axial profiles of oxygen pressure ($PO_2$) in the rat retina from capillary $sO_2$ showing trends that parallel the changes in inhaled oxygen concentration. Retina depth: 0%: ILM, 100%: BM.

DETAILED DESCRIPTION

Figure 1:
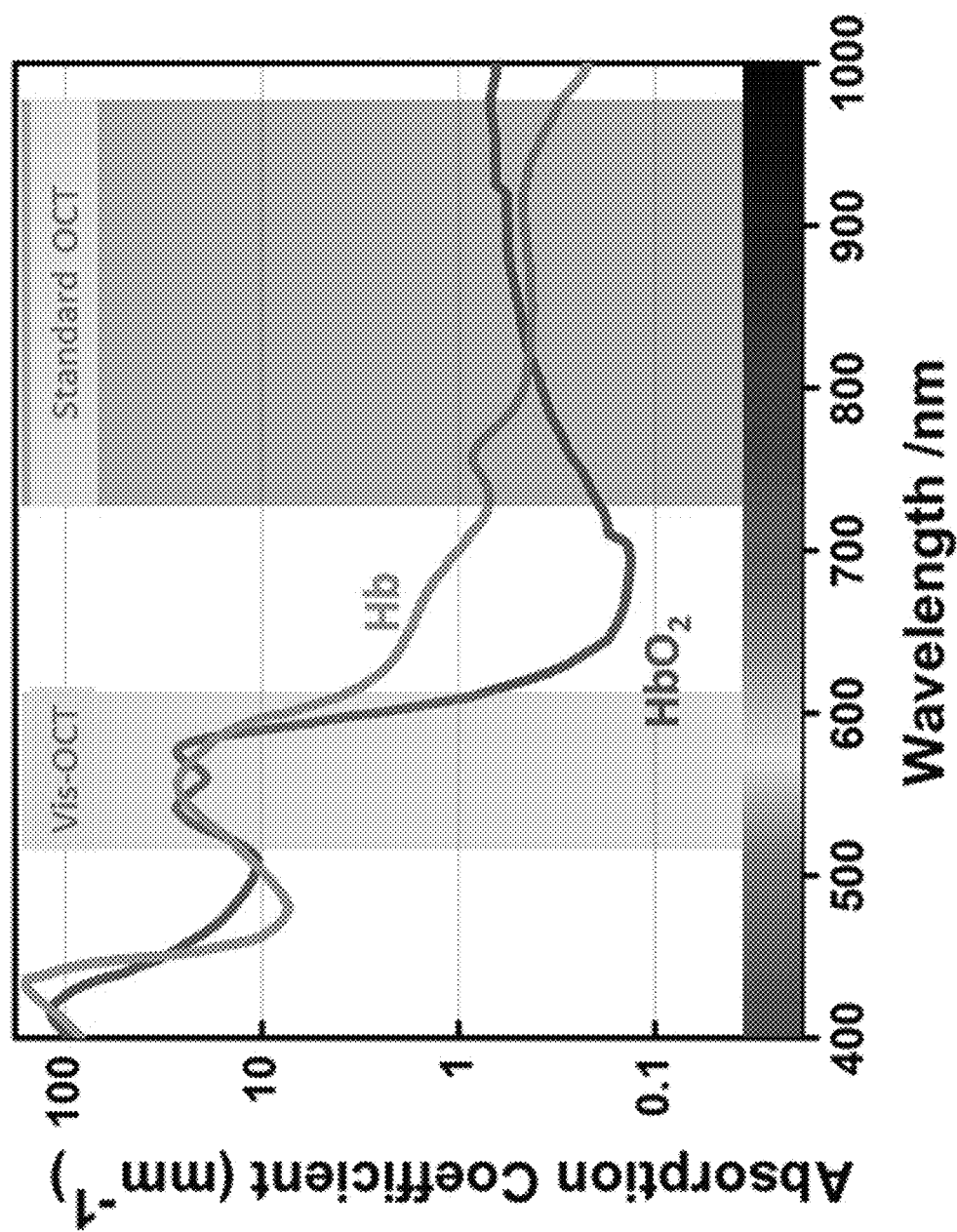
FIG. 1 is a graph illustrating Logarithmic absorption extinction coefficients of oxygenated hemoglobin (HbO2) and deoxygenated hemoglobin (Hb) in the wavelength range from 400 nm to 1000 nm. The much higher extinction coefficients in the visible range (vis-OCT) compared to the infrared range (standard OCT) provides better contrast to quantify oxygen saturation ($sO_2$).

Disclosed are methods and systems for capillary oximetry using optical coherence tomography (OCT). In some embodiments, the capillary oximetry may be performed on a retina (retinal capillary oximetry).

Also disclosed herein is an exemplary system for acquiring and performing capillary oximetry using the disclosed methods. The exemplary system comprises an OCT device configured to acquire OCT structural and angiography data in functional connection with a computing device having a logic subsystem and data holding capabilities. In embodiments the computing device is configured to receive data from the OCT device and perform one or more operations of the methods described herein.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCT angiography (OCTA) and associated techniques for characterizing blood flow, Doppler OCT, polarization-sensitive OCT, OCT elastography, spectroscopic OCT, differential absorption OCT, and molecular imaging OCT.

Disclosed herein are methods and systems for capillary oximetry (e.g., retinal capillary oximetry) using OCT. The method may include one or more of: obtaining an OCT angiography dataset; performing capillary segmentation based on the OCT angiography dataset to obtain capillary segments; resampling, registering, and/or averaging B-scans of the OCT angiography dataset that correspond to a first capillary segment of the capillary segments to obtain an averaged B-scan for the first capillary segment; determining an anterior and posterior border of the first capillary segment; and determining an oxygen saturation of the first capillary segment based on the averaged B-scan, the anterior border, and the posterior border.

OCT is an imaging technology of great utility in ophthalmology due to its ability to provide label-free, high-resolution, 3-dimensional images of the retina. Standard OCT has been explored for oximetry by using the isosbestic point, which occurs around 800 nm, of oxygenated and deoxygenated hemoglobin. However, this approach has limited accuracy, since extinction due to light absorption in the near infrared is overwhelmed by scattering.

In various embodiments, visible light OCT (vis-OCT) may be used to quantify $sO_2$ in the retina for the much higher absorption coefficients of hemoglobin in the visible range, achieving a superior performance over standard OCT. Compared to standard OCT operating in the near infrared, vis-OCT provides several advantages for blood oxygen saturation measurement. For example, FIG. 1 illustrates logarithmic absorption extinction coefficients of oxygenated hemoglobin (HbO2) and deoxygenated hemoglobin (Hb) in the wavelength range from 400 nm to 1000 nm. First, the extinction coefficients of $HbO_2$ and Hb are two-orders of magnitude stronger in the visible range than in the infrared, thereby providing better contrast to quantify oxygen saturation $sO_2$. Second, confounding absorption from water molecules is nearly absent in the visible range. Third, the absorption characteristics of $HbO_2$ and Hb have much better contrast for spectroscopic analysis in the visible range, showing remarkable peaks that can be distinguished on the logarithm extinction coefficient curve ($HbO_2$: 540 nm and 575 nm, Hb: 555 nm).

As vessels can be isolated in the depth profile (A-line) with high axial and transverse resolution, the absorption spectrum at the posterior vessel borders, where the signal-to-noise ratio is largest, can be used for optimal $sO_2$ measurements. The reasons for this are 1) the accumulated absorption is greatest in the posterior vessel boundary, and 2) the reflectance signal is usually strong due to the strong reflection of vessel wall. A fiber-based compact vis-OCT system may be used for high-resolution structural and angiographic imaging. The present inventors have used this system to implement a non-invasive spectroscopic retinal oximetry algorithm for blood $sO_2$ in the major vessels of rat retinas by exploiting the automated detection of the vascular posterior boundary on structural OCT cross-sections (B-scans).

Although retinal capillaries have been successfully visualized in angiographic images with visible light OCT, oximetry in these capillaries has not been achieved previously. Capillary oximetry is especially difficult because of the much reduced caliber and much larger tortuosity of capillaries compared to major vessels. However, the $sO_2$ level in capillaries is ultra-important for understanding the metabolism of the retina and predicting its pathologies. Moreover, as capillaries pervade more predominantly throughout tissue, pathologies that locally alter metabolism may present earlier in capillaries than in major vessels. Pathological changes in capillaries may also appear earlier than structural changes or vascular degeneration/angiogenesis.

In this disclosure, a method is described that can reliably measure the $sO_2$ in a single capillary, as well as improve $sO_2$ measurement accuracy in major vessels. Although some embodiments utilize spectroscopic fitting to calculate the $sO_2$, it is also applicable when using the optical density ratio to enhance measurement accuracy. In addition, while the techniques are discussed herein in the context of retinal images, the method is also applicable to blood circulations in other ocular tissue (such as the iris) and non-ocular tissue (such as cerebral cortex).

Various aspects of the disclosed techniques are described in more detail below. For example, a system configuration of the visible light OCT is shown and described. Additionally, an aspect may include generating the angiography and segment the capillaries volumetrically or in en face projection images. Another aspect may include resampling and registering a series of B-scans along the capillary centerline in x-y plane from the volumetric dataset. A further aspect may include performing an effective posterior voxel detection algorithm on the averaged B-scans to locate the bottom of capillaries. Another aspect may include applying a spectroscopic fitting algorithm to the OCT spectrum to resolve the $sO_2$. Furthermore, shown and described herein are results of retinal capillary oximetry in the rat retina and a demonstration of the corresponding response of the vascular/capillary plexus to the regulation of inhaled oxygen concentration (normoxia/hypoxia/hyperoxia).

The techniques introduced herein may quantify the oxygen saturation in a single capillary in a non-invasive, dye-free way. The disclosure provides both a system and method as further described below.

Figure 2:
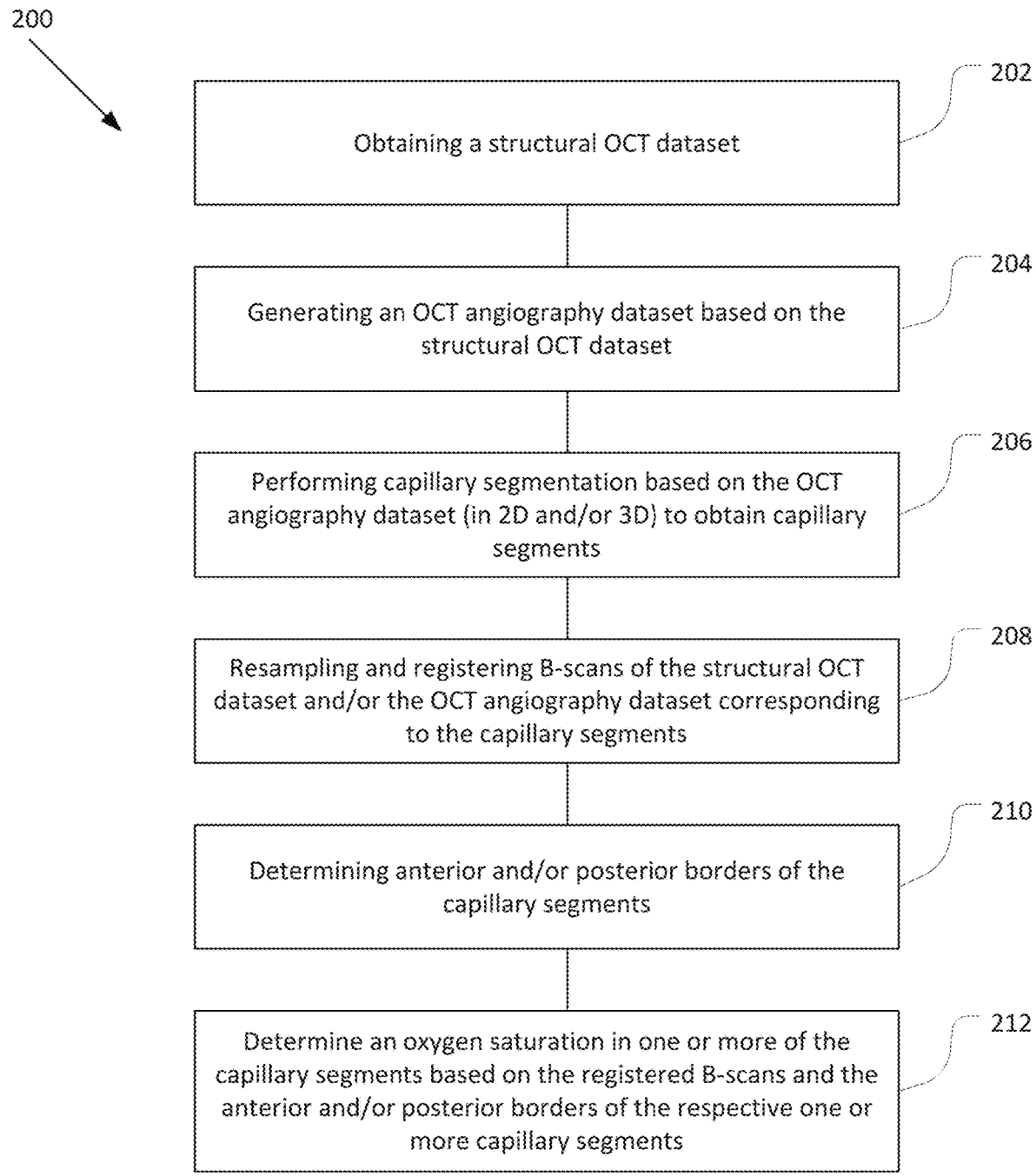
FIG. 2 is a flowchart to illustrate a method for capillary oximetry of a sample using OCT, in accordance with various embodiments.

For example, FIG. 2 illustrates a method 200 for capillary oximetry (determining the oxygen saturation in one or more capillaries) of a sample (e.g., a retina or another suitable sample of biological tissue), in accordance with various embodiments. One or more aspects of the method 200 may be performed by an OCT system, as discussed further herein.

At 202, the method 200 may include obtaining a structural OCT dataset. For example, the OCT dataset may be obtained by scanning the sample with visible light by an OCT system.

At 204, the method 200 may include generating an OCT angiography dataset from the structural OCT dataset.

At 206, the method 200 may include performing capillary segmentation based on the OCT angiography dataset to obtain capillary segments. The capillary segmentation may be performed in 2-dimensions (e.g., based on en face projections of the OCT angiography dataset) and/or in 3-dimensions (e.g., based on the volumetric OCT angiography dataset), as discussed further herein.

At 208, the method 200 may include resampling and registering B-scans of the structural OCT dataset and/or the OCT angiography dataset that correspond to the capillary segments. In some embodiments, the method 200 may further include averaging the registered B-scans along individual capillary segments to obtain an averaged B-scan for the individual capillary segment.

At 210, the method 200 may include determining anterior and/or posterior borders of the respective capillary segments, e.g., based on the registered/averaged angiographic B-scans and/or the structural B-scans.

At 212, the method 200 may include determining an oxygen saturation in one or more of the capillary segments based on the registered B-scans (e.g., the averaged B-scan) and the anterior and/or posterior borders of the respective one or more capillary segments.

Further detail and/or example implementations of various aspects of the method 200 are described below.

1. Fiber-Based Visible Light OCT System

Figure 3:
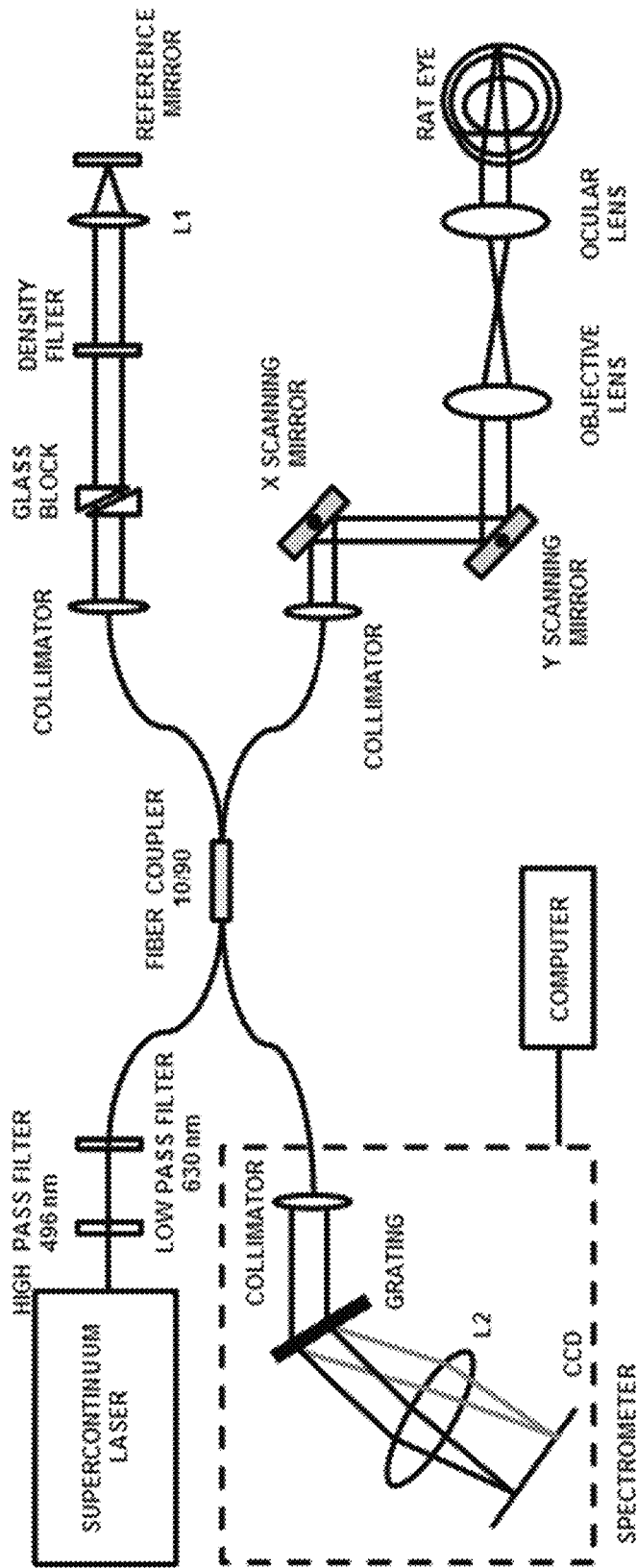
FIG. 3 schematically illustrates an OCT system that may be used in accordance with various embodiments.

FIG. 3 illustrates an example visible light OCT system in accordance with various embodiments. A super-continuum white light laser delivers ultra-broad and steady illumination over a range of 1200 nm. The light is first filtered by a short-pass and a long-pass edge filter pair, and coupled into a wideband fiber optic coupler. One light beam travels to the sample arm illuminating a sample (e.g., bio-tissue such as the retina, skin, or cerebral cortex). The other light beam travels to the reference arm and is reflected by a protected silver mirror. Achromatic protected silver reflective collimators couple the light into free space at each arm of the interferometer. A pair of triangular glass blocks placed in the reference arm with adjustable thickness allow the system to adapt dispersion mismatch between the two beams to different samples. The reference power is further attenuated by a variable neutral density filter to prevent saturation of the CMOS sensor.

In the sample arm, galvo mirrors steer the light over a squared region on the sample. A telescope formed by an objective lens and ocular lens is used to direct the beam to the retina. For other tissues, a scan lens can focus the light. Imaging can be performed without physical contact with the tissue. The light collected from the sample and reference arms is spatially dispersed by an 1800 lines/mm transmission grating and captured by a line scan camera connected to a frame grabber. Hardware synchronization and data acquisition may be controlled by custom software (e.g., written in C language through a multifunction data acquisition card). The wavelength may be calibrated with a Neon calibration light source.

During one exposure time, light illuminates one spot on the retina. The reflected light at different depths causes different interferogram patterns. By performing a fast Fourier transform on the interferogram recorded by a spectrometer, a depth-resolved profile of the tissue reflectance, called an A-line, is acquired. By rotating the scanning mirrors, the illumination can be guided to different spots. When moving in the fast scanning direction, a series of A-lines can be captured to form a B-scan (i.e., a 2D image plane). Multiple B-scans in a slow scanning direction form a volumetric scan, which can be used to provide a perspective visualization of retina.

It will be apparent that modifications to the OCT system shown in FIG. 3 may be made in accordance with various embodiments, including additional components, omitting one or more components, and/or including different components.

2. Capillary Segmentation

The angiogram may be generated from the reflectance data using the split-spectrum amplitude-decorrelation angiography (SSADA) algorithm (e.g., as described in Jia Y, Tan O, Tokayer J, et al. Split-spectrum amplitude-decorrelation angiography with optical coherence tomography. *Optics express*. 2012; 20(4):4710-4725, hereby incorporated by reference). Briefly, the algorithm splits the full spectrum into multiple bands and calculates the decorrelation value among subsequent B-scans at each band. By averaging the signal across each of the bands, image contrast is greatly improved and noise levels reduced. Additionally, the SSADA algorithm has demonstrated clinical utility, and is used by commercial instruments. It is therefore an excellent choice of method for generating angiograms in this system as it is both an established and powerful technique.

2.1 2-D En Face Segmentation

For capillary segmentation in en face images, retinal layer segmentation may be performed. In some embodiments, this may be performed with a graph-search technique on structural B-scan images. The laminar vascular/capillary plexuses (see FIG. 4A) are then generated by projecting the angiogram signal within specific slabs. For the superficial vascular plexus (SVP), a slab containing the nerve fiber layer (NFL) and ganglion cell layer (GCL) may be used. For the intermediate capillary plexus (ICP) and deep capillary plexus (DCP), slabs corresponding the upper and lower boundaries of the inner nuclear layer (INL), respectively, may be used.

After the en face projections are created, vessel binary masks (as shown in FIG. 4B) may be obtained by thresholding the flow signal in the angiogram. In some embodiments, morphological processing may also be applied to ensure that only the blood circulation network is retained in the image. After that, the binary masks are transformed to a skeleton (as shown in FIG. 4C) to delineate the vascular centerline. The resulting skeletonized image contains only information about the vascular architecture, without regard to vessel size. An important feature of the vascular skeleton is that it can differentiate vascular end-points, body-points, bifurcation-points, and overlay-points. To accomplish this goal, a neighbor-counting filter that returns the number of vascular pixels bordering a pixel may be applied to the skeletonized image. As described in Eq. (1), vascular pixels with just one neighboring vascular pixel are vascular end-points. If the pixel instead has two neighboring vascular pixels, it means the vasculature is continuous and the pixel is a body-point. If the pixel has three neighboring vascular pixels, it means there is a bifurcation. Finally, if the pixel has four or more neighboring vascular pixels, two or more vessels are overlaid in the en face projection, and the pixel is an overlay point.

$$\text{Number of neighboring vascular pixels} \begin{cases} N = 1, & \text{end-point} \\ N = 2, & \text{body-point} \\ N = 3, & \text{bifurcation-point} \\ N \geq 4, & \text{overlay-point} \end{cases} \quad (1)$$

To extract capillary segments, the bifurcation- and overlay-points in the skeleton (marked by red dots in FIG. 4C) may be removed. The capillary segment is then isolated with each other. The transverse X-Y positions could be detected through image processing techniques, which treats each contiguous region as separate objects and reveal the locations of pixels in each object. The final capillary segmentation result is shown in FIG. 4D, with the normal direction of capillary (yellow arrows) calculated at each body-point as the angle of the X- and Y-gradient in the smoothed centerline for B-scan resampling.

2.2 3-D Volumetric Segmentation

Figure 5B:
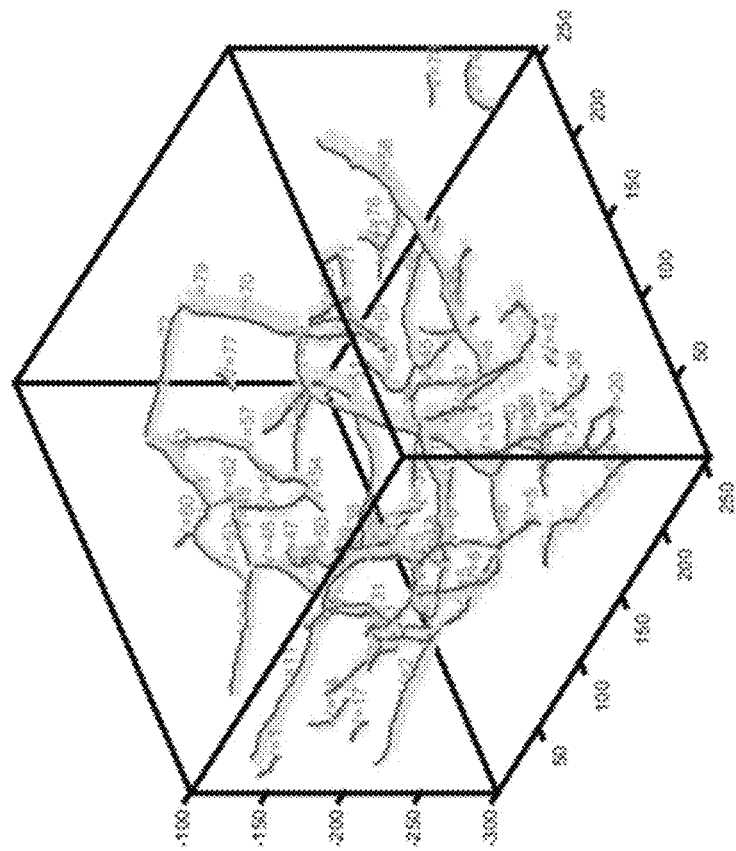
FIGS. 5A and 5B illustrate vascular segmentation in 3-dimensional (3-D) volume.
Figure 5A:
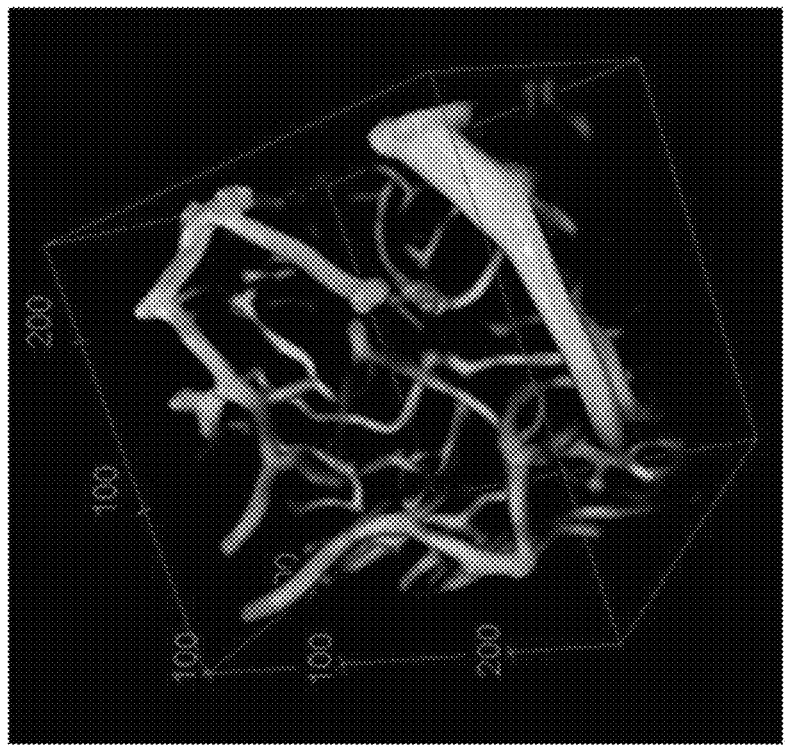

Since the retinal vasculature pervades three dimensionally, and it can be resolved by OCT angiography volumetrically, the capillary segmentation may also be obtained directly in 3-D. To accomplish this, the original angiogram may be processed with a projection-resolved OCTA (PR-OCTA) algorithm (e.g., the PR-OCTA algorithm described in Wang J, Zhang M, Hwang T S, et al. Reflectance-based projection-resolved optical coherence tomography angiography. *Biomedical optics express.* 2017; 8(3):1536-1548, hereby incorporated by reference), a regression bulk motion subtraction algorithm (e.g., the regression bulk motion subtraction algorithm described in Camino A, Jia Y, Liu G, Wang J, Huang D. Regression-based algorithm for bulk motion subtraction in optical coherence tomography angiography. *Biomedical optics express.* 2017; 8(6):3053-3066, hereby incorporated by reference), and may be further enhanced with a 3-D vesselness filter (e.g. the vesselness filter described in Frangi A F, Niessen W J, Vincken K L, Viergever M A. Multiscale vessel enhancement filtering. Paper presented at: International conference on medical image computing and computer-assisted intervention, 1998, hereby incorporated by reference). In this way, the entire angiogram volume (see FIG. 5A) is selected for processing and retinal layer segmentation is unnecessary.

A 3-D skeleton can be obtained in a fashion similar to a 2-D skeleton. Another small adjustment changes the neighbor-counting filter from 2D to its 3D analog. As in the 2D case, bifurcation and overlay points may be identified on the skeletonized image for exclusion. The normal direction of capillary may be calculated in three dimensions from the gradient.

3. B-Scan Resampling and Registration

After the capillary segmentation, reconstructed B-scans may be resampled along the capillary normal direction, with transverse position centered on vascular pixels in skeleton for both the structure and angiography volumes. The reconstructed B-scans (see FIGS. 6A-6E) cover all axial pixels and an axial range near the vessel depth position. The B-scans in the volumetric dataset are first aligned to get rid of the animal motions. After that, the reconstructed B-scans are registered axially to one reference frame (such as the first frame in each capillary segment) to align the vessels in each frame. The shifts of each frame in axial direction are recorded for later image reconstruction. All registered B-scans along one capillary segment are then averaged in structural image and the angiogram to extract the capillary cross-sectional region.

4. Axial Border Detection

The averaged angiographic B-scan and structural B-scan may then be flattened to the internal limiting membrane (ILM) boundaries for further processing. The anterior border of the capillary segment may be determined in the angiogram B-scan by comparing the flow profile to a threshold value. Since the reconstructed B-scans are resampled along the capillary segment and averaged, the signal from other capillaries and noise are largely suppressed and only the signal from the specific capillary segment is enhanced. The angiogram profiles may be compared with a threshold to find the start of the angiogram profiles at the anterior borders of the capillary segment. The posterior border of the capillary segment may be achieved in the averaged, reconstructed structural B-scans. Usually, vascular pixels have stronger reflectance than neighboring tissues due to the large scattering of red blood cells, whereas the pixels underneath vascular pixels have much lower reflectance (or dark shadows) than neighboring tissues due to severe absorption of hemoglobin in visible light range. The posterior border of the capillary segment is obtained by finding the zero-crossing position in the difference axial profile ($A_d$) of the averaged capillary A-line profile ($A_c$) and the averaged A-line profile for the entire B-scan ($A_a$) (see FIGS. 6A-6E). After that, the vascular axial caliber may be calculated as the distance of these two (anterior and posterior) borders. The results may also be applied back to all frames in the reconstructed B-scans to create or assist modification of the 3-D mask of capillary segments, together with transverse x-, y-positions.

5. Spectroscopic Fitting

In OCT, the spatial- and depth-resolved optical density OD (z, λ) may be defined as the logarithm of the ratio of the reflected intensity spectrum I (z, λ) to the source spectrum $I_0$ (λ). It stands for the reflectivity at a certain illumination wavelength for the tissue at a certain depth and can be expressed as Eq. (2) based on a modified Beer's law.

$$OD(z, \lambda) = \ln\left(\frac{I(z, \lambda)}{I_0(\lambda)}\right) = \qquad (2)$$
$$-2(z - z_0)[C_{HbO_2}\varepsilon_{HbO_2}(\lambda) + C_{Hb}\varepsilon_{Hb}(\lambda)] - \alpha\ln(\lambda) + \ln(AR_0)$$

Here, $z_0$ and z are the depth of anterior and posterior voxels respectively, and $z-z_0$ is the accumulated absorption length for the capillary. The scattering spectrum of the vessel wall r(λ) can be modeled as a power law $A \cdot \lambda^{-\alpha}$ under the first-order Born approximation (e.g., as described in Yi J, Backman V. Imaging a full set of optical scattering properties of biological tissue by inverse spectroscopic optical coherence tomography. *Optics letters.* 2012; 37(21):4443-4445, hereby incorporated by reference). The scattering spectrum at the reference arm $R_0$ is considered as a wavelength-independent constant. The subscript $HbO_2$ and Hb indicate the contribution from oxygenated and deoxygenated hemoglobin respectively, with their extinction coefficients ε referring to the literature values, and concentrations C being calculated by fitting. The oxygen saturation is then determined as $sO_2 = C_{HbO2}/(C_{HbO2} + C_{Hb})$.

The OD (z, λ) can be extracted by short time Fourier transform (STFT) spectroscopic analysis of the interference fringes at the detected vascular posterior voxels. For example, a Gaussian window with a full-width at half-maximum of approximately 9 nm and an interval distance around 3 nm may be applied, resulting in 21 split spectral bands in total. In some embodiments, only those bands within a contrast region (e.g., from 527 nm to 582 nm) may be selected for linear regression fitting.

6. Capillary Order

Figures 11A, 11B, 11C:
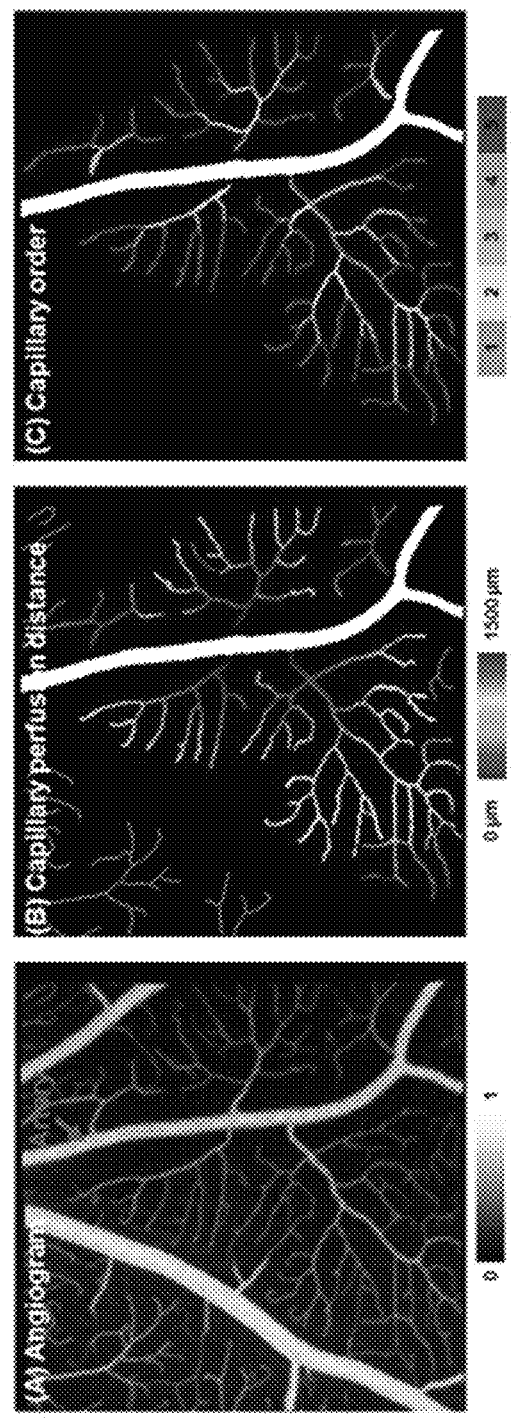
FIG. 11A illustrates an angiogram.
FIG. 11B illustrates a capillary perfusion distances map.
FIG. 11C illustrates a capillary order, respectively, for pre-capillary branches from a major artery in the superficial vascular plexus (SVP).

The capillary perfusion distance may calculated to quantify the pathway length for a capillary segment to be perfused by the major vessels (see FIG. 11A). The metric may be defined as the shortest distance between a capillary segment to the major vessel through the vascular network. In some embodiments, the shortest distance may be determined by using the weighted shortest path problem model. Specifically, the identified capillary segments may be assigned as nodes for the model and the identified bifurcation-points may be used to construct a connection graph. For each bifurcation-point, six interconnection channels may be built between the three neighboring capillary segments nodes. The weight of each connection channel $P_{ij}$ is the mean capillary lengths of the $i^{th}$ and $j^{th}$ capillary segments. After establishing the connection graph, the capillary segments that branched directly from the major vessels may be identified by visually inspecting the en face images (see FIG. 11A). Then, the capillary perfusion distances of all capillary segments may be calculated as the shortest path distances to these direct-branched capillary segments. The node list of their shortest pathway may also be recorded. It should be noted that, in some cases, the capillary perfusion distance for some capillary segments may not be obtained due to the limited field of view (see FIG. 11B).

By establishing the shortest pathway for a capillary segment to reach a major vessel, its relative location along the circulatory network may be determined. For each bifurcation, a capillary must have the smallest perfusion distance, and so be the closest capillary segment to the artery. Such capillaries may be identified as the parent branch at a bifurcation. The other two capillary segments with larger perfusion distance may then be identified as the children branches. For each capillary segment, its upstream capillary segments may be determined as the nodes in its perfusion pathway, and its downstream capillary segments may be determined by searching in which capillary segment perfusion pathway it occurred. The flow-inlet and flow-outlet of each capillary segment may be determined to reveal blood flow direction by comparing the distances of two end-points to the upstream and downstream capillary segment. After that, the distance along the blood flow direction may be used to generate the pixel wise capillary perfusion distance map shown in FIG. 11B.

Capillary order may be further quantified for each capillary segment by counting the number of downstream capillary segments. As shown in FIG. 11C, the capillary segments may be determined as first order (e.g., count larger than 20, magenta), second order (e.g., count between 19 and 8, yellow), third order (e.g., count between 7 and 3, cyan), and fourth order (e.g., count between 2 and 1, green) capillary segments respectively. The capillary segments without downstream capillary segment may be identified as fifth order capillary segments (count 0, blue).

7. Results in Retinal Capillary

Figure 7:
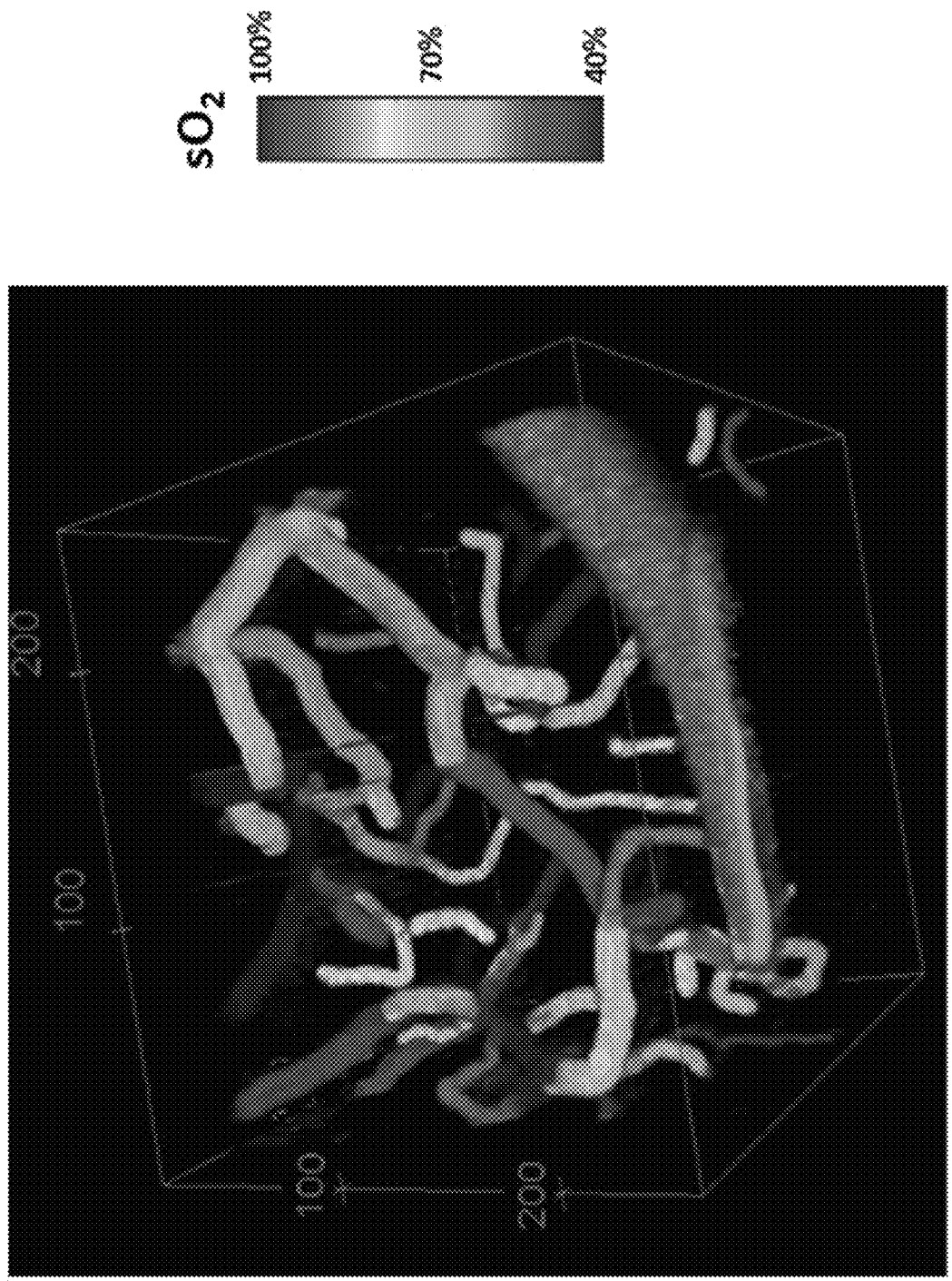
FIG. 7 illustrates results of capillary oxygen saturation illustrated in volumetric visualization.

An example result of the retinal capillary oximetry techniques described herein is shown in FIG. 7. The volumetric scan was acquired from a Brown Norway rat retina at normal air condition. The image field was about 0.3 mm×1 mm×1 mm in the z-, x- and y-directions. The capillary segmentation was accomplished in 3-D. The oxygen saturation, as well as the vascular organization of the three plexuses was revealed.

Figure 8:
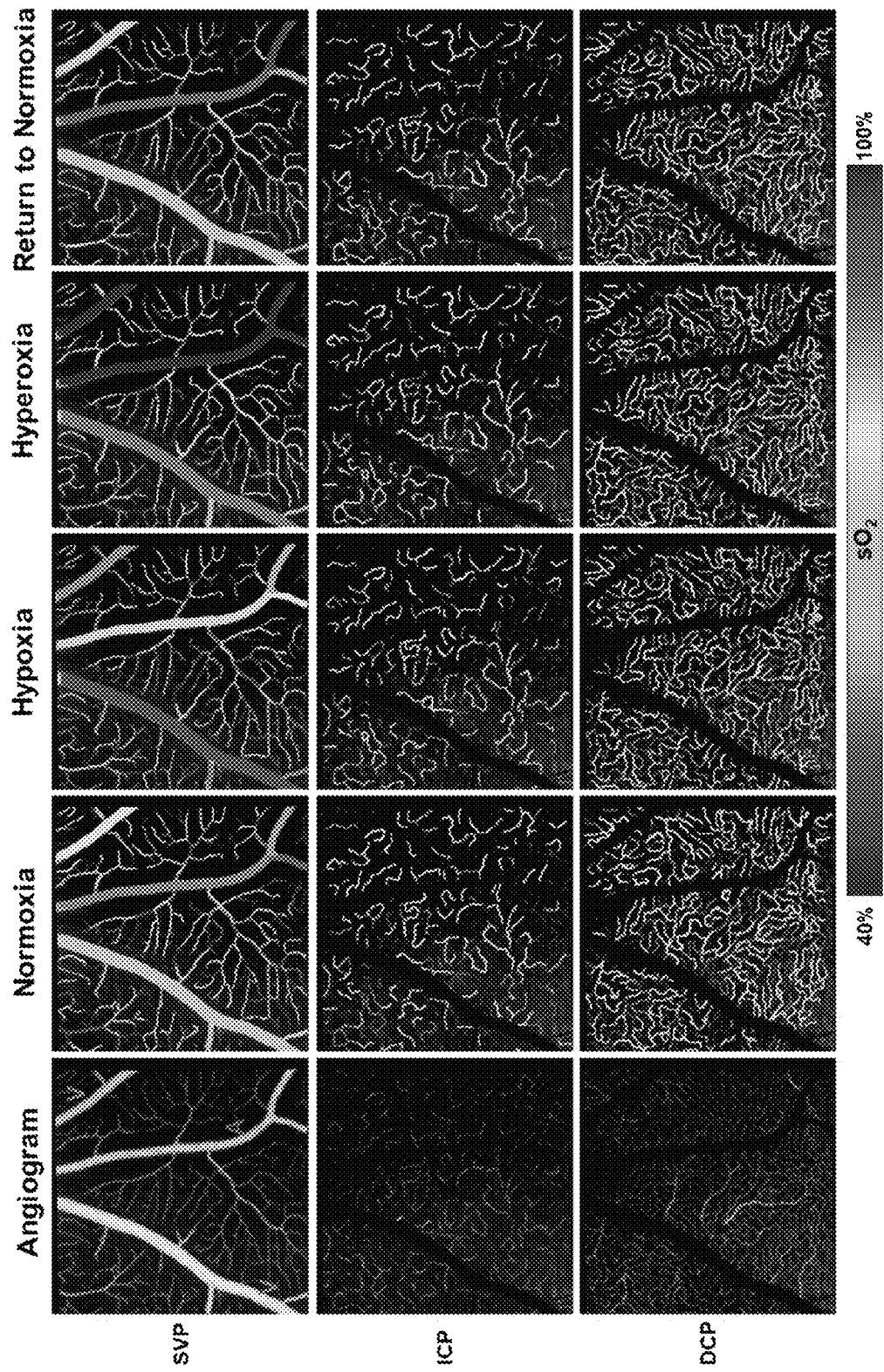
FIG. 8 illustrates results of capillary oxygen saturation in three vascular plexuses during regulation of inhaled oxygen concentration from normoxia to hypoxia to hyperoxia, and back to normoxia.

The performance of retinal capillary oximetry was further validated by regulating the inhaled oxygen concentration of the rat. First, normal air (21% $O_2$) was ventilated to the rat under anesthesia. After that, the oxygen concentration was reduced to 15% to create a hypoxic condition. As shown in FIG. 8, the oxygen saturation in both major vessels and capillaries was reduced, corresponding to the established physiological observation. After that, the oxygen concentration was increased to 100% to create a hyperoxic condition. The oxygen saturation in both the major vessels and capillaries show a remarkable increase. The measured oxygen saturation resumed when the animal was return to normoxia condition. These results at different conditions indicated that retina capillary oximetry can record the oxygen saturation down to a single capillary level in exceptional detail.

8. Additional Experimental Results

Further experimental results are provided below, which may be associated with and/or extensions of the embodiments/results discussed above. For example, the experiment may be an extension of the results described above in Section 7.

Altered retinal metabolism contributes to neural and vascular cell apoptosis, which is implicated in many ocular diseases but is highly challenging to measure. The experimental results presented herein provide an in vivo assessment of hemoglobin oxygenation across the full vascular transition from retinal arteries to capillaries to retinal veins in rats using visible-light optical coherence tomography, and demonstrate physiologic responses to alterations in the concentration of inhaled oxygen. This non-invasive technique provides access to capillary $sO_2$, an important factor required for determining local retinal oxygen metabolism in rodent disease models. Operating within the safety level allowed by ANSI standards for humans, this has strong potential to benefit research on ocular vascular biology and physiology and influence clinical management of patients with retinal disease.

8.1 Introduction

The retina consists of layers of neurons and glial cells that transduce light into electrochemical impulses with which the brain produces visual cognition and perception. The high metabolic demand of this neurosensory tissue is supported by an intricate retinal vasculature that is organized into several laminar plexuses. Abnormalities in retinal microvascular anatomy, along with alterations in the blood-retinal barrier and blood flow, play a crucial role in various ocular diseases. Furthermore, alterations in blood oxygen saturation ($sO_2$, the fraction of oxygenated hemoglobin relative to total hemoglobin in blood vessels) are believed to be an early predictive biomarker for ocular diseases. Measurement of retinal $sO_2$, called retinal oximetry, relies on the distinctive molar extinction coefficients of oxygenated and deoxygenated hemoglobin across a wide optical spectral range.

Oximetry can provide crucial insights into retinal metabolism[6], and many studies indicate the role of $sO_2$ in retinal pathology. However, oximetry on just retinal arteries and veins may not provide information on oxygenation of specific tissue layers or regional changes in metabolism, which may occur in some conditions, such as glaucoma, retinal vascular occlusion or diabetic retinopathy. This will require information from individual capillary beds. Until recently, retinal capillary oximetry has remained inaccessible due to the limited spatial resolution of available imaging modalities such as fundus photography and photoacoustic microscopy. An indirect way to achieve such detail by measuring the partial pressure of oxygen ($PO_2$) using two-photon microscopy[16] and computing $sO_2$ based on the Hill equation has been successfully used to measure $pO_2$ in cerebral capillaries. However, several problems limit the application of this approach to the retina. These include increased difficulty in focusing in the eye and the need to use light power that is beyond the tissue safety level.

Optical coherence tomography (OCT) has revolutionized ophthalmic imaging by providing detailed, depth-resolved information on tissue structure. Recently, the development of OCT angiography has enabled in vivo, non-invasive visualization of the retinal vasculature down to the capillary level, and quantitative studies have shown that alterations in retinal capillary morphology can indicate pathology earlier than changes in tissue anatomy. Compared to standard OCT operating in the near infrared band, visible-light OCT (vis-OCT) produces higher axial resolution and higher spectral contrast between oxy- and deoxy-hemoglobin. Using vis-OCT, oximetry on major vessels in rodents and humans has been successfully demonstrated and used to monitor how progressive hypoxic challenge or intraocular pressure (IOP) elevation affects retinal oxygen metabolism. Advances in automated detection of posterior vascular boundaries, acquisition of multiple circumpapillary scans, and quantitative quality-controls have been made to improve retinal oximetry on major vessels.

Described herein is a reliable method for measuring retinal capillary $sO_2$ utilizing vis-OCT. The experimental results present an in vivo assessment of hemoglobin oxygenation across the entire retinal vascular tree in rats for the first time. The experimental results also investigate the distribution of $sO_2$ in the different retinal vessel and capillary beds and how this responds to changes in inspired oxygen concentration.

8.2 Results 8.2.1 Morphology of the Retinal Microcirculation in the Rat

Three laminar vascular/capillary plexuses—the superficial vascular plexus (SVP), intermediate capillary plexus (ICP), and deep capillary plexus (DCP)—were projected to en face images from their respective depth slabs (see FIGS. 12A-12G). Compared to humans, retinal vascular patterns in rats are less dense and do not demonstrate radial peripapillary capillaries. Due to the much higher hemoglobin absorption of visible light, shadows underneath vessels are much darker in vis-OCT than in standard OCT. In addition, projection artifacts from the SVP to deeper capillary networks, common in standard OCT, were absent in the ICP and DCP due to a stronger backscattering signal and weaker forward multiple-scattering of the visible band.

$sO_2$ measurements in major vessels can distinguish arteries (red) from veins (green) (FIG. 12E)[29]. By tracing the vascular network from major vessels in en face images, arterial capillaries were found to occur predominantly in the SVP (see FIGS. 12B, 15A-15C), whereas veins tended to drain blood from the DCP (FIGS. 12D, 15A-15C. Within the SVP, a few direct connections were noted between arteries and veins, making it possible to classify capillaries in this layer, by whether they were connected to arteries or veins (FIGS. 1B and 8). For the purpose of analyzing $sO_2$, these capillaries were designated as either arterial or venous, since their responses might differ from each other. A similar capillary designation was not possible for the ICP and DCP capillaries, since these were less discrete than the SVP. As capillary segments of ICP appeared to terminate frequently in the en face image, the ICP was suggested to serve as a bridging plexus between the SVP and DCP in the rat retina.

As the three laminar vascular plexuses are located parallel to each other, but in different retinal layers, vertical inter-plexus capillaries are essential to form a connected network. Since inter-plexus capillaries are perpendicular to the retinal layers and have greater absorption length along the direction of light illumination, they appeared as dark spots in structural en face OCT (see FIG. 12E). Inter-plexus capillaries were further identified by observing their presence in overlaid en face angiograms of the three vascular/capillary plexuses (see FIG. 12F). These inter-plexus capillaries were frequently found at the distal ends (turning points to deeper plexuses) of superficial capillaries, as well as in some bifurcations (see FIGS. 15A-15C).

Figures 12A, 12B, 12C, 12D, 12E:
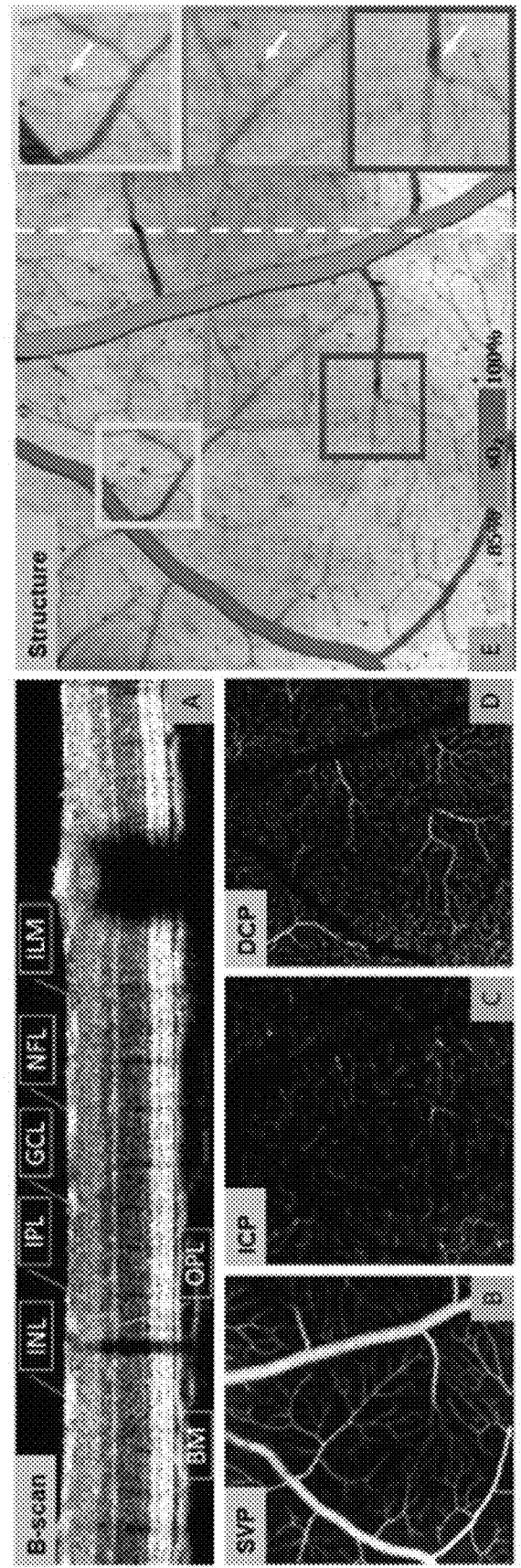
FIG. 12A is a B-scan image of a brown Norway rat retina using visible-light OCT. ILM: inner limiting membrane, NFL: nerve fiber layer, GCL: ganglion cell layer, IPL: inner plexiform layer, INL: inner nuclear layer, OPL: outer plexiform layer, BM: Bruch's membrane.
FIGS. 12B, 12C, and 12D are en face images of vascular/capillary plexuses. SVP: superficial vascular plexus projected in the NFL and GCL slabs. ICP: intermediate capillary plexus projected in the slab containing the inner border of the INL. DCP: deep capillary plexus projected in the slab containing the outer border of the INL.
FIG. 12E is an en face structural image projected from the ILM to BM, overlaid with measured oxygen saturation ($sO_2$) values in major vessels in order to differentiate arteries from veins in an animal breathing 100% $O_2$. Inter-plexus capillaries (white arrows) appear as dark spots due to greater light absorption than neighboring capillaries.
Figures 12F, 12G:
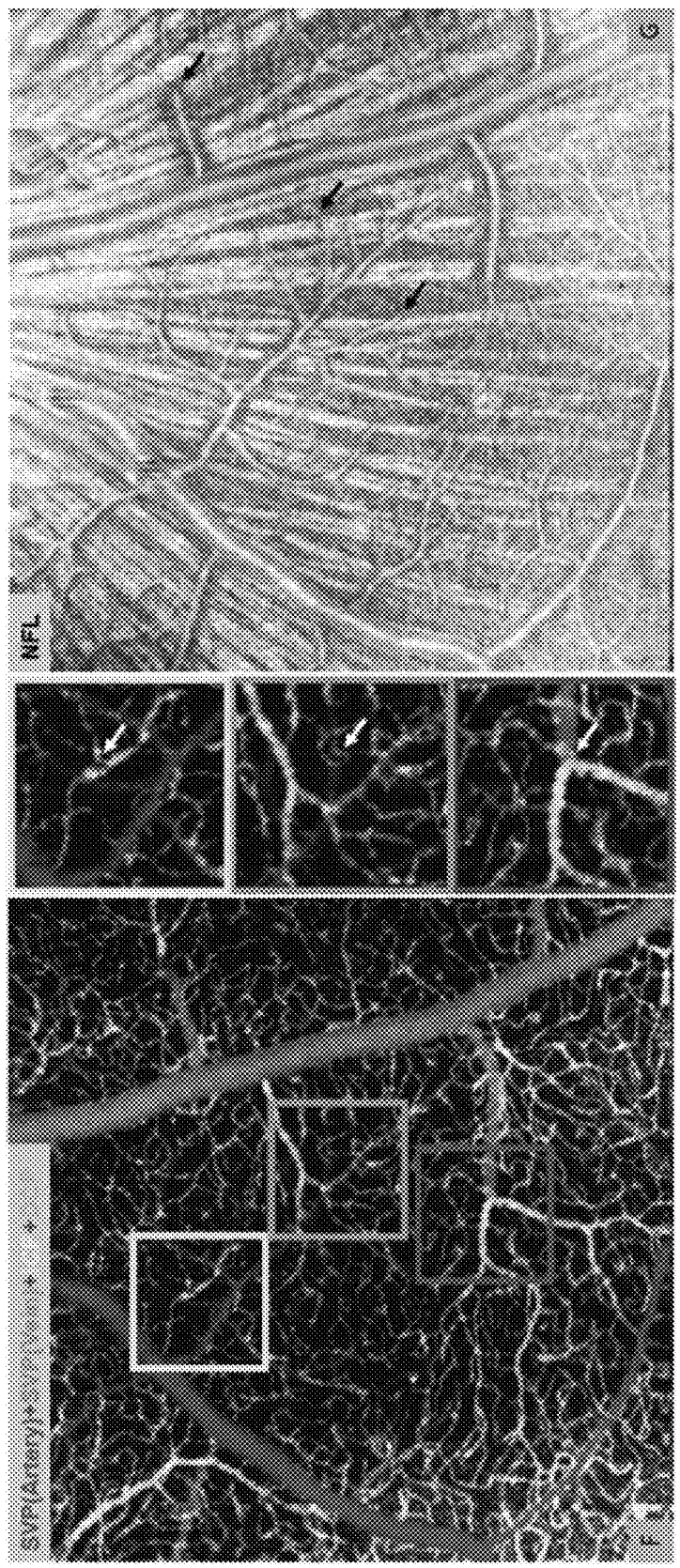
FIG. 12F is an overlaid en face angiograms of three vascular/capillary plexuses to demonstrate the detailed organization of the retinal circulation. Examples of inter-plexus capillaries (indicated by white arrows in the enlarged images) were validated by observing their presence in corresponding locations.
FIG. 12G is an en face projection of the NFL slab. The SVP was found to run anterior to the nerve fiber bundles (bright radial striations), which appear posterior to the vessels. The inter-plexus capillaries (black arrows) penetrate between NFL bundles and connect the SVP to the ICP and DCP.
Figure 16:
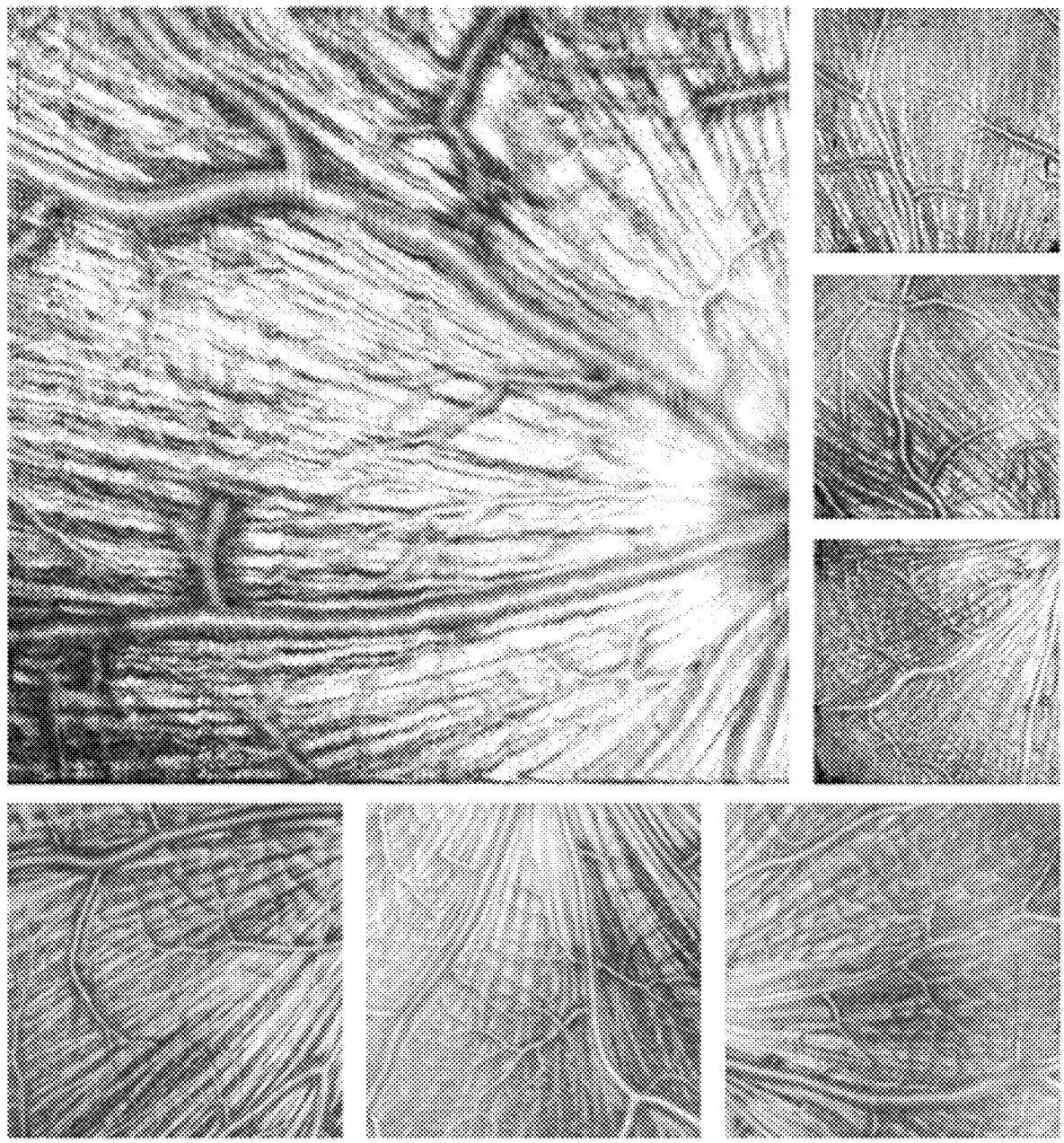
FIG. 16 illustrates en face projections of the nerve fiber slab at various regions of different rat retinas show that the superficial vascular plexus runs anterior to the never fiber bundles.

Owing to the high resolution of vis-OCT, the nerve fiber bundles could be clearly visualized in en face images by projecting the structural reflectance signal in the nerve fiber layer (see FIG. 12G). They appeared as bright radial striations running from the retinal periphery towards the optic disc. Gaps between the nerve fiber bundles gradually tapered as the fibers coalesced while approaching the optic nerve head. The SVP can be visualized anterior to the nerve fiber bundles in the en face image, with inter-plexus capillaries penetrating gaps between bundles (see FIGS. 12G and 16).

8.2.2 Retinal Microcirculatory $sO_2$.

Figure 17:
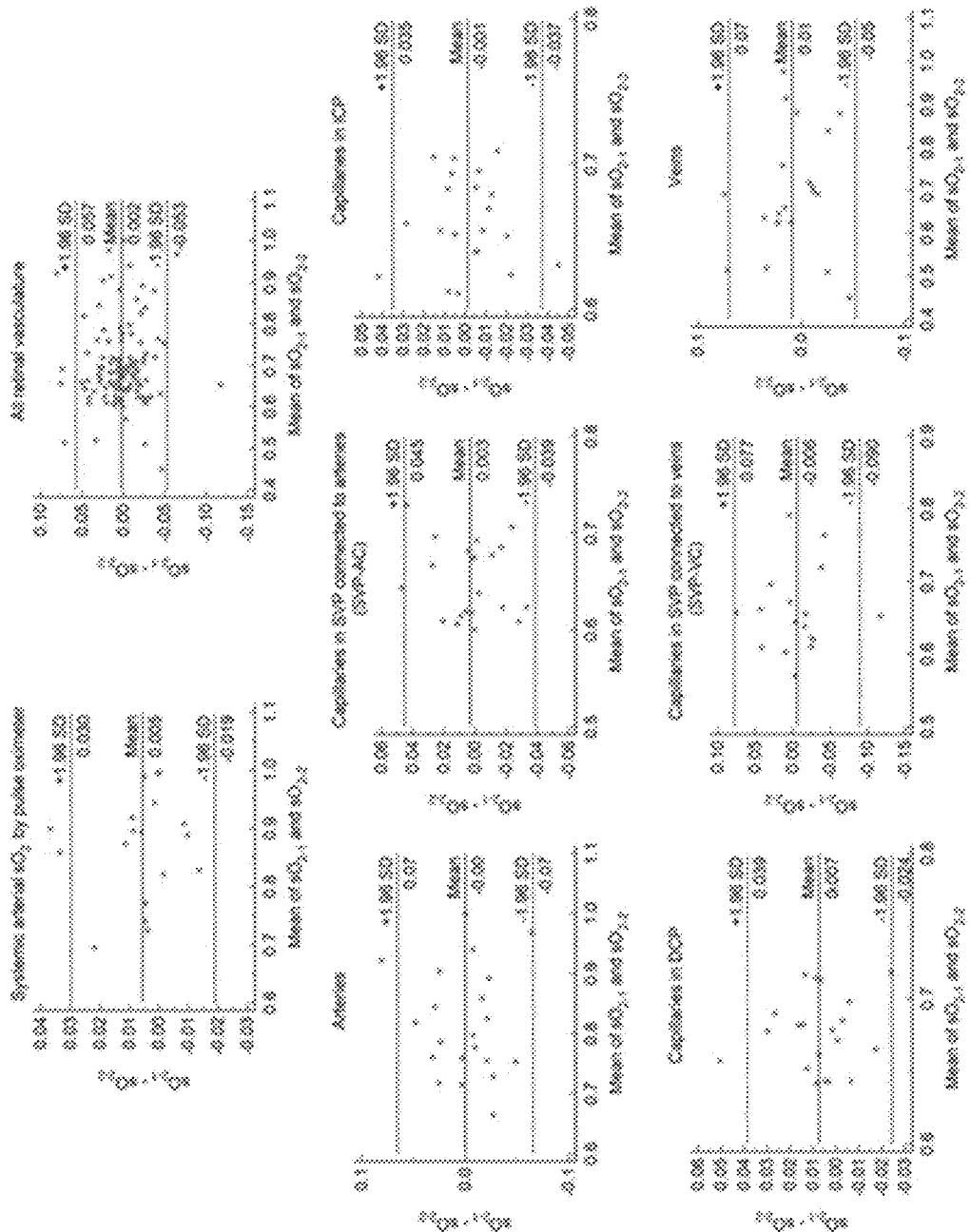
FIG. 17 shows Bland-altman plots showing the repeatability of systemic arterial oxygen saturation ($sO_2$) by pulse oximeter, and OCT oximetry-measured $sO_2$ for different vascular plexuses between the first session ($sO_{2-1}$) and the second session ($sO_{2-2}$).

Using the algorithm described in the Methods section below, the $sO_2$ in retinal capillaries, as well as that in retinal arteries and veins, could be measured in vivo. The $sO_2$ in major vessels was similar to that reported earlier, with corresponding levels in capillaries. $sO_2$ of major vessels as well as capillaries was noted to change in response to changes in inspired $O_2$ (see FIG. 8). The $sO_2$ results between two measurement sessions (see FIG. 13A) in each plexus at all conditions were repeatable, as shown by a Bland-Altman analysis (see FIG. 17). The mean difference between measured $sO_2$ in two sessions was 0.2%±2.6%, with a Pearson correlation coefficient of 0.96 (p-value<0.01). The inter-scan repeatability (pooled standard deviation) was calculated as 1.9% of absolute $sO_2$.

The measured retinal arterial $sO_2$ correlated well with the systemic $sO_2$, and the $sO_2$ in veins was lower than that in arteries (see FIG. 13B). The averaged $sO_2$ in the SVP capillaries connected to arteries (SVP-AC), ICP capillaries and DCP capillaries were all similar, and all were lower than that in arteries (see FIG. 13B). Distinctively, venous $sO_2$ could be lower or higher than capillary $sO_2$, depending on the inhalation conditions. In addition, the $sO_2$ in SVP capillaries connected to veins (SVP-VC) was different than the values in other capillaries, possibly due to the extensive presence of large caliber venules, which may function more like retinal veins (see FIG. 13C).

Figure 18:
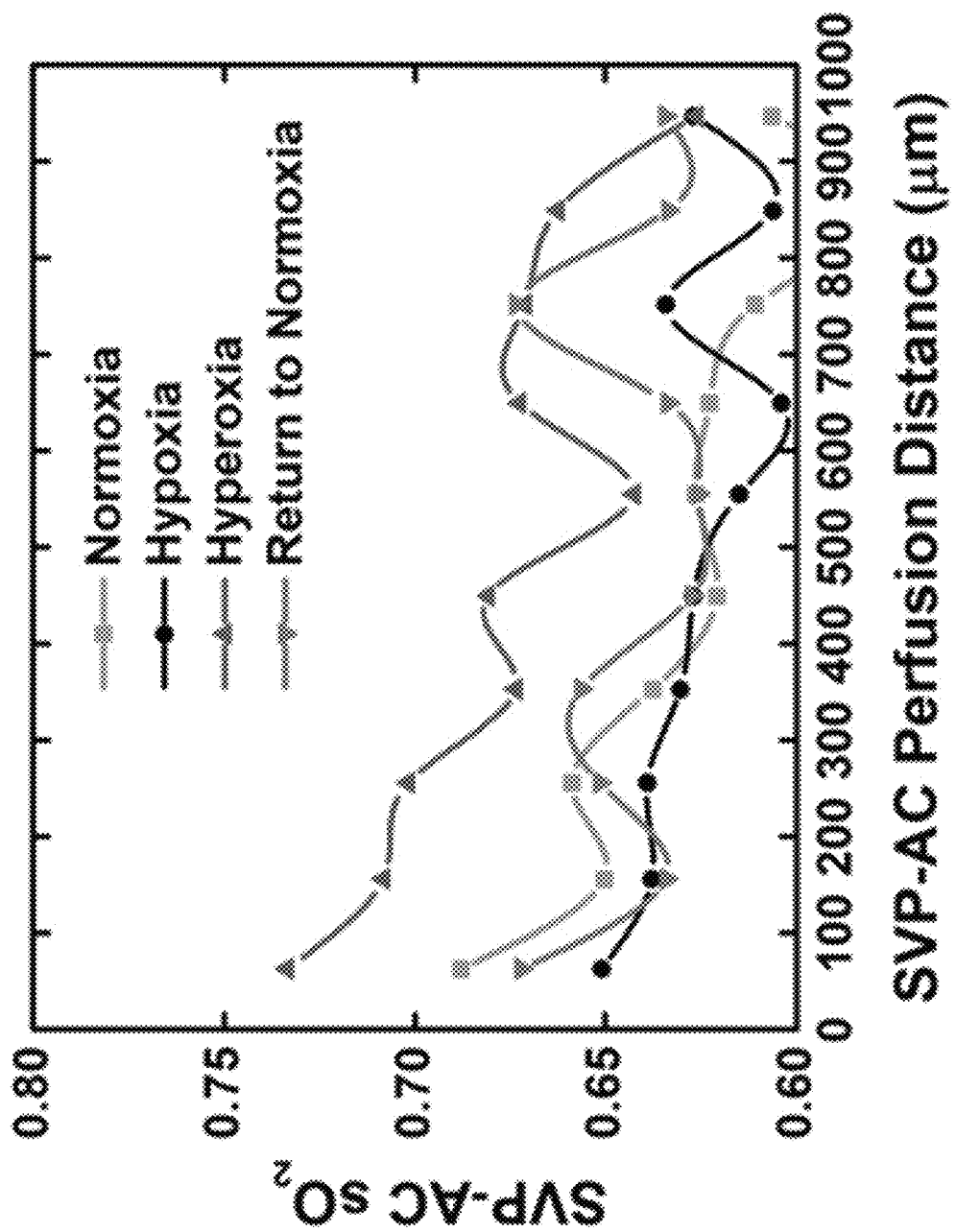
FIG. 18 is a plot of the $sO_2$ in SVP arterial capillaries (SVP-AC) versus perfusion distance, showing that the $sO_2$ in SVP-AC decreases with increasing perfusion distance.

To investigate the distribution of $sO_2$ along perfusion paths more specifically, the levels of $sO_2$ by capillary order were examined in SVP arterial capillaries, in which successive tributaries of capillaries arising from larger arterial vessels could be easily traced. The capillary order was determined by the abundance of branches in the network (see Methods section below). First order capillaries, which might in fact be arterioles, were directly connected with retinal arteries and had a larger caliber than their downstream vessels. $sO_2$ in these vessels was closer to the values in retinal arteries than that of successive capillary orders (see FIG. 13D). At progressively higher orders, the caliber of capillary segments decreased and perfusion distance increased (see the Methods section below). Overall, $sO_2$ decreased gradually with increasing capillary order (see FIG. 13D), consistent with a release of oxygen to tissues along these capillaries. In fifth order capillaries, $sO_2$ was maintained at almost the same level as that in the ICP and DCP. As expected, increased capillary perfusion distance, which was positively correlated with capillary order, was associated with a decrease in $sO_2$ (see FIG. 18).

8.2.3 Retinal Microcirculatory $sO_2$ Responses to Hypoxia/Hyperoxia.

Overall, $sO_2$ in the retinal circulation decreased during hypoxia, increased during hyperoxia, and returned to normal when conditions returned to normoxia (see FIG. 8 and FIG. 13C). However, the extent of these responses was not identical in the different plexuses. Venous $sO_2$ changed most dramatically (see FIGS. 13B-13C) from a low of 52.5%±5.7% in hypoxia, to a high of 85.3%±6.0% in hyperoxia. The oxygen extraction, calculated as the difference between arterial and venous $sO_2$, was ~20% in normoxia and hypoxia, and reduced to ~14% in hyperoxia.

Compared to the $sO_2$ in major vessels, the $sO_2$ in capillaries changed less during inhaled oxygen regulation. For the SVP arterial capillaries, ICP capillaries, and DCP capillaries, the absolute value of $sO_2$ decreased by ~2% (p-value<0.01) in hypoxia and increased by ~4% (p-value<0.01) in hyperoxia, as compared to an $sO_2$ of ~65% in normoxia.

8.3 Discussion

Assessing capillary oxygen saturation is desirable but challenging. First, as the spectral contrast from absorption increases with the vertical propagation of light into deeper retinal layers, capillaries become much harder to identify, due to their small caliber and reduced accumulation of spectral contrast. Second, there are fewer blood cells than in major vessels, and their passage is intermittent, leading to a discrete, stochastic signal. Finally, it is difficult to accurately determine the axial location of each capillary. Previously, oxygen saturation in major retinal vessels was achieved. The possibility of performing capillary oximetry by spectral contrast using a backscattering-based image modality like OCT has been demonstrated through numerical simulations and was recently achieved using dual-band, dual-scan inverse spectroscopic OCT in the mouse ear. However, capillary oximetry in the retina is more challenging, given the optical aberrations presented by the eye and more strict safety limitation on laser illumination in the eye than in other tissue. In this work, the ultra-high resolution of vis-OCT allowed visualization of the three vascular plexuses in the retinal circulation clearly, as well as individual nerve fiber bundles, which has not been possible previously without using adaptive optics to correct for aberrations.

As shown herein, retinal capillary oximetry is demonstrated by effectively extracting the spectroscopic signal from each capillary segment. As can be seen in FIG. 8, $sO_2$ values can be obtained from almost all capillary segments. The failure of capillary oximetry, which occurred on only ~2% capillary segments, was mainly due to problems with posterior vessel border detection. As expected, transient $sO_2$ fluctuations in capillaries, associated with the random passage of individual erythrocytes, were observed between capillary segments and within individual segments between scans. The reliability of the algorithm was supported by good inter-scan repeatability, and demonstration of an expected reduction in $sO_2$ along SVP capillaries with known perfusion pathways.

Capillaries are the major site of $O_2$ delivery to local tissue. Given this, reduced $sO_2$ along the blood flow path would be anticipated. We found that capillary $sO_2$ decreases with increasing capillary order within the SVP for arterial capillaries, consistent with decreased oxygen pressure ($PO_2$) observed by two photon microscopy in cerebral blood circulation. These findings suggest that oxygen delivery is occurring along capillaries in the SVP. Interestingly, we did not observe further changes in $sO_2$ between fifth order capillaries, and those of the ICP and DCP. The significance of this finding at present is uncertain, as the anatomic relationships between the ICP and DCP capillary beds are complicated and not fully understood. Further work using this technology is warranted to help clarify the role of the ICP and DCP in delivering oxygen to the deeper layers of the retina.

Capillary $sO_2$ is not a direct measure of local tissue ischemia. However, this can be used to calculate tissue oxygenation. Since retinal tissue oxygen is supplied by diffusion from capillaries, one can first convert measured $sO_2$ to oxygen pressure in the capillaries using the oxygen-hemoglobin dissociation curve and then, from this, calculate oxygen diffusion from capillaries to the retinal tissue using Fick's law (see Methods section below). The resulting calculation reveals distinct levels of tissue oxygen pressure in different layers of the retina (see FIGS. 23A-23C) in a pattern that strongly parallels a published axial profile of tissue oxygen pressure measured by invasive oxygen-sensitive microelectrodes in the rat. This not only demonstrates that tissue oxygenation can be derived from capillary $sO_2$, it illustrates that capillary $sO_2$ can provide level-specific information on retinal oxygenation. This could be particularly valuable in diseases where some layers of the retina are preferentially damaged, as in glaucoma, which primarily affects the nerve fiber layer and retinal ganglion cells and in which inner retinal capillary drop-out has been documented.

Figures 19A, 19B, 19C:
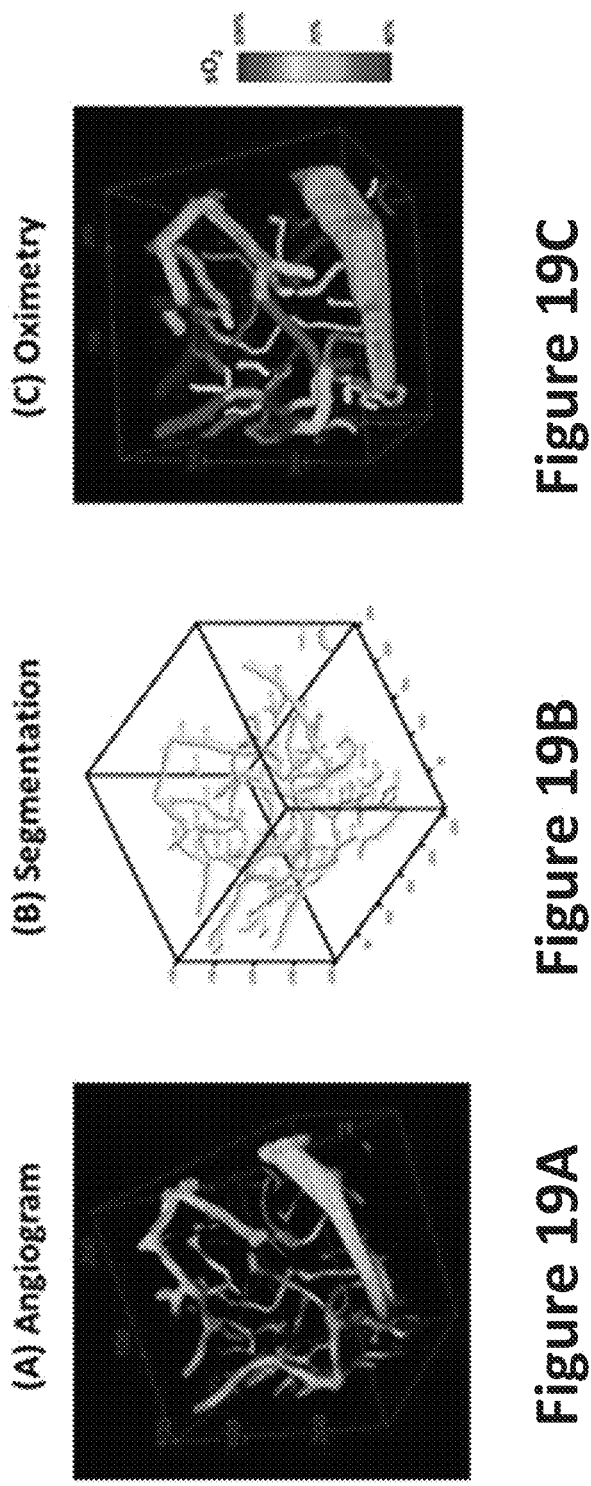
FIGS. 19A, 19B, and 19C illustrate capillary oximetry performed volumetrically with a 0.5×0.5-mm field of view.

In this initial model, each capillary plexus was simplified to a single layer diffusion source, which limits calculated diffusion to the axial dimension. In additional refinements, the true 3-D positions of each vessel may be resolved (demonstrated in FIGS. 19A-19C), allowing to locate them as diffusion sources of oxygen. The locations of these vessels in 3 dimensions may enable determination of lateral, as well as axial diffusion. In this manner, measurements of capillary $sO_2$ will lead to non-invasive generation of 3-D retinal tissue maps of oxygen pressure. This may be particularly valuable in vaso-occlusive diseases, such as diabetes and vascular occlusion, which may result in local reductions in tissue oxygenation or potentially, as in the case of retinal vein occlusion, increases in post-capillary venules produced by bypass via collateral vessels.

As expected, systemic $sO_2$ and that in major retinal arteries and veins varied in parallel with the concentration of inspired $O_2$. However, there were relatively small changes in retinal capillary $sO_2$ under conditions of hypoxia and hyperoxia. Although not confirmed by the present inventors in animals using an alternative method, reports using microelectrodes have noted a similarly muted response in oxygen tension to hyperoxia in the inner 50% of the rat retina, which, as shown in FIGS. 23A-23C, corresponds to the SVP, ICP and DCP. Interestingly, long-term oxygen exposure in rabbits, which lack this control, can produce severe retinal degeneration. The results presented herein, obtained in young adult animals, likely reflect the ability of a healthy retinal microcirculation to maintain a stable source of oxygen delivery when challenged by changing systemic oxygen conditions.

An additional finding is that, while $sO_2$ in veins was equivalent to that in capillaries when exposed to normoxic conditions, this increased, and was higher than that in capillaries in hyperoxia. This may be due to the discrepancy between the length-weighted mean capillary $sO_2$ (the calculated averaged capillary $sO_2$ in this study) and the flow-weighted mean capillary $sO_2$ (closer to $sO_2$ in veins). In this situation, capillaries with faster flow (which would tend to have a higher oxygen saturation due to less oxygen extraction along their path) might contribute more blood to the veins. Testing this, as well as understanding how autoregulation contributes to the control of inner retinal oxygen tension in hyperoxia, will require the ability to measure blood velocity in individual capillary segments. This may be possible with further optimization of the vis-OCT algorithm described herein.

In some embodiments, to reduce discomfort (as may accompany photoreceptor bleaching) during retinal imaging in awake humans, using a lower power illumination (e.g., <0.22 mW) than the ANSI standard may be more clinically acceptable. This may in turn affect image quality and measurements of capillary $sO_2$. Additionally, because the human eye has a longer focal length than the rat, the light beam at the pupil would need to be enlarged for retinal imaging in humans in order to maintain the same lateral resolution. While the instrument used in this example implementation provides a 20°×20° field of view, significantly wider fields can be obtained by post-processing, as shown in supplemental FIG. 15C.

While the technique described herein does not yet provide velocimetric data for individual capillary segments, it is believed that this will be possible with further refinements in vis-OCT. Since blood flow velocity in conjunction with $sO_2$ determines the oxygen transport rate within specific vessels, this information, applied to 3-D capillary maps, can be used to determine regional changes in oxygen metabolism in specific tissue beds. The vis-OCT capillary oximetry method demonstrated here is an important step in achieving this capability.

Accordingly, the embodiments described herein acquired high-resolution, three-dimensional images of rodent retinas with vis-OCT, and calculated $sO_2$ along capillary segments by fitting their respective spectroscopic signals. In contrast to the human retina, it was found that the superficial vascular plexus runs anterior to the nerve fiber bundles and that the inter-plexus capillaries penetrate the gaps between nerve fibers to connect with the ICP and DCP. From en face angiograms of the vascular plexuses, it was determined the perfusion pathway, length, centerline and normal directions of capillary segments in the SVP and further quantified the perfusion distance and order for arterial capillaries in this layer. Embodiments achieve retinal capillary oximetry in the three vascular plexuses in the rat retina, and further describe the $sO_2$ distribution pattern along the blood flow transition pathway from major retinal arteries to major retinal veins, as well as the physiological responses to hypoxic and hyperoxic conditions. Use of this technology and its expansion to determine 3-D tissue maps of oxygenation along with velocimetry will help to clarify and expand understanding of the retinal oxygen supply in health and disease.

8.4 Methods 8.4.1 Animal Preparation.

Six wild type brown Norway rats (14 weeks old) were included in this study. The animals were initially anesthetized with 5% isoflurane in a sealed box for 10 minutes, followed by 2.5% isoflurane mixed with inhalation gas during imaging. After anesthesia, the animal was immobilized in a custom-made imaging stage with multidimensional manipulation for alignment. The right eyes of animals were selected for imaging, yielding a total of six eyes for statistical analysis. The pupil was dilated with a 1% tropicamide ophthalmic solution before imaging. To keep the cornea moisturized, sterile irrigating salt solution (Alcon Laboratories Inc.) was applied to the eye every other minute. The animal's body temperature was maintained with a 38.5° C. using a water-warming blanket. The exhaust gas was removed by a vacuum pump to avoid carbon dioxide and excess isoflurane accumulation and collected by an anesthesia gas filter (OMNICON F/air, Bickford) before releasing to the open air.

During imaging, the oxygen concentration in the inhalation gas was regulated from normoxia (21% $O_2$), to hypoxia (15% $O_2$), to hyperoxia (100% $O_2$), and returned to normoxia. Oxygen regulation was achieved by changing the ratio of the pure oxygen, normal air, and nitrogen with the total gas flow rate maintained at approximately 1 L/min, with oxygen concentration monitored by a calibrated oxygen analyzer (MiniOX I, Ohio Medical Corporation). The systemic arterial oxy-hemoglobin saturation ($SaO_2$), respiration rate and pulse were recorded by a pulse oximeter (MouseOx Plus, STARR) attached to the left rear paw of the animal. In general, the respiratory rate was ~45 breaths per minute in normoxia, increased to ~70 in hypoxia and decreased to ~35 in hyperoxia. For each condition, the animal was allowed to rest for 3~5 minutes, and imaged only after the $SaO_2$ reading stabilized. In general, the animal was maintained at each condition for about 6 minutes. All observations were completed for each animal in about 30 minutes.

8.4.2 OCT Image Acquisition.

The vis-OCT used here is a custom-built prototype housed in the Center for Ophthalmic Optics & Lasers laboratory (COOL LAB) of OHSU's Casey Eye Institute. The illumination spectrum covered the high absorption contrast region of hemoglobin from 510 nm to 610 nm ($\lambda_c$=560 nm, full width at half maximum (FWHM) was ~90 nm) and was calibrated with a neon calibration light source (NE-1, Ocean Optics). The dispersion mismatch between the two arms was compensated both physically and numerically. An unbalanced 90:10 wideband fiber optical coupler delivered 10% power into the sample arm (power=0.8 mW, which is within the safety level of laser power allowed by ANSI standards). A telescope tube ($f_1$=75 mm, $f_2$=11 mm) guided light into the eye. The system operated at a flexible axial scan sampling rate and scanning angle, with a 1.2-μm axial resolution and approximately 6-μm lateral resolution with an image depth of 1.8 mm. The maximum sensitivity was measured as 89 dB with a protected silver mirror.

Two repeated volumetric raster scans were collected near the optic disc with a field of view of 2×2-mm at each inhalation condition. Each scan consisted of 512 axial profiles in the fast transverse scanning direction to form a B-scan, with 3 repeated B-scans at each slow transverse scanning direction and 512 slow transverse scanning positions. The acquisition for each volumetric scan was completed within 17 seconds at a sampling rate of 50 kHz. The recorded interferogram was processed for OCT structure and the SSADA algorithm was used for OCT angiography. Layer segmentation was done with a graph-search technique on structural B-scan images. The laminar vascular/capillary plexuses were then generated by projecting the flow signal within specific slabs. Registration was performed for en face images at all conditions acquired at the same region, and the images were then averaged to improve the signal-to-noise-ratio.

8.4.3 Capillary Segment Extraction.

Using en face OCT angiograms (FIG. 14A) from each vascular plexus, vessel binary masks (FIG. 14B) were obtained by thresholding frangi-vesselness-filter enhanced angiograms. Six binary masks were created for each eye, including four in the SVP for retinal arteries, capillaries connected to arteries (SVP-AC in Results), capillaries connected to veins (SVP-VC in Results), retinal veins, as well as two for capillaries in the ICP and DCP, respectively. All binary masks were skeletonized (FIG. 14C) using a thinning algorithm to delineate the vascular centerline, collapsing vascular caliber information and preserving only the connectivity. The vascular points in the skeleton were further differentiated as vascular end-points, body-points, bifurcation-points, and overlay-points by counting the number of neighboring vascular pixels N. Specifically, the capillary end-points had only N=1 neighboring point, body-points had N=2 neighboring points, bifurcation-points had N=3, and overlay-points had N greater than or equal to 4.

To extract capillary segments, all bifurcation- and overlay-points (red dots in FIG. 14C) were removed from the skeleton. The capillary segments were then isolated from each other (capillary segment, green text in FIG. 14D), with the coordinates of the centerline read from the image (red scatter line in FIG. 14D). Based on the coordinates, capillary normal directions (yellow arrows in FIG. 14D), capillary segment length, and capillary orientation could be determined. Together with vessel binary masks (FIG. 14B), capillary segment binary masks and capillary calibers could also be determined. It should be noted that the capillary segmentation could also be performed volumetrically prior to retinal layer segmentation (see FIGS. 19A-19C).

9.4.4 Posterior Capillary Border Detection.

After extracting capillary segments (see FIG. 6A), a series of reconstructed B-scans (see FIG. 6B) were resampled on both the structural and angiographic volumes along the capillary normal directions, with the transverse positions centered on the centerline. Before resampling, the original B-scans were first aligned according to the center of mass of the averaged axial profile to reduce the effect of animal motion. After that, the reconstructed B-scans were registered to one reference frame (we used the middle frame in each capillary segment). The shifts in each A-line were recorded for later spectroscopic processing. All registered structural and angiographic B-scans along the capillary segment were then averaged to extract the capillary anterior and posterior borders described below (see FIG. 6C).

Figure 20:
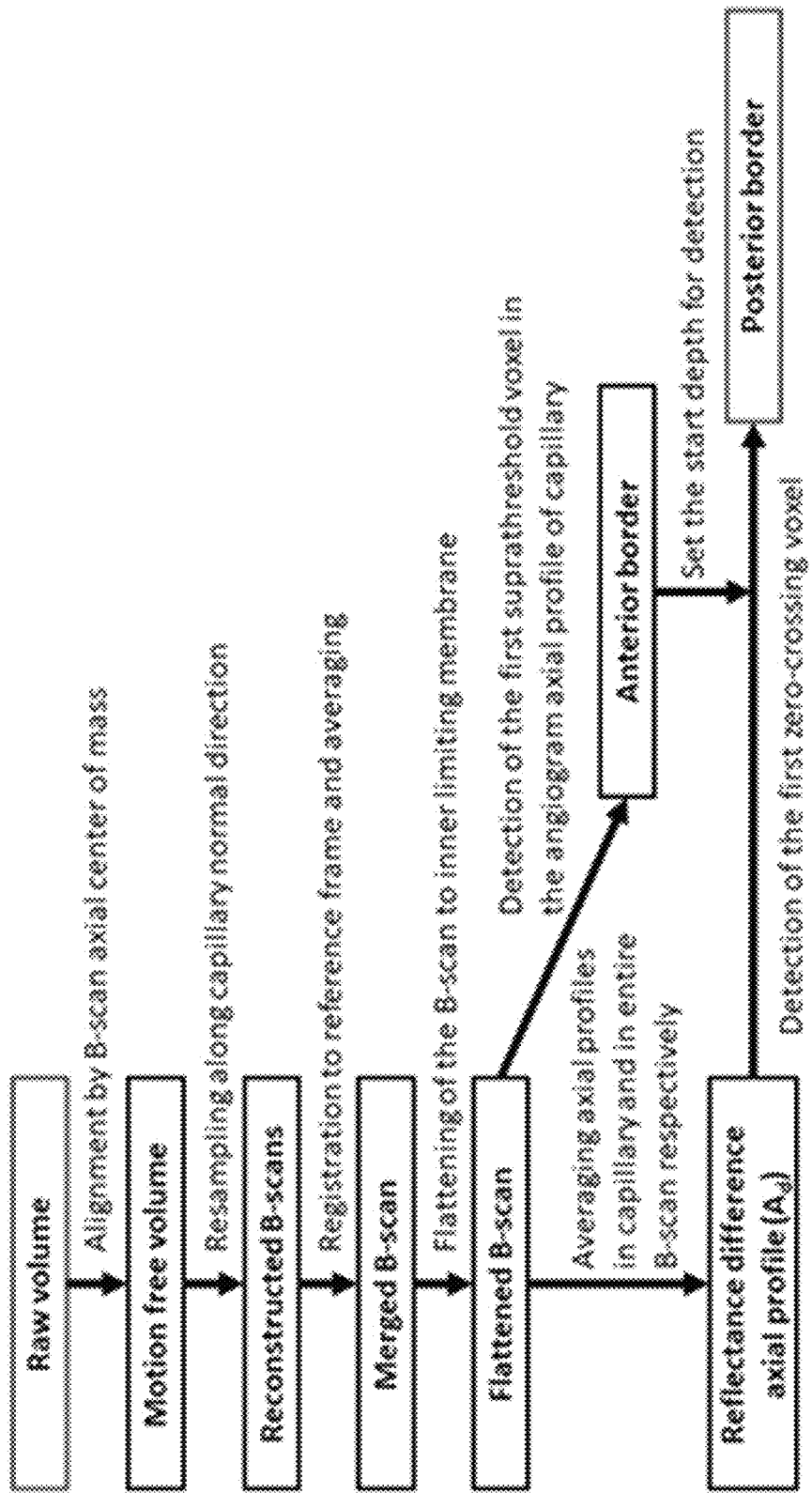
FIG. 20 is a schematic diagram of a posterior capillary border detection process in accordance with various embodiments.
Figures 21A, 21B, 21C:
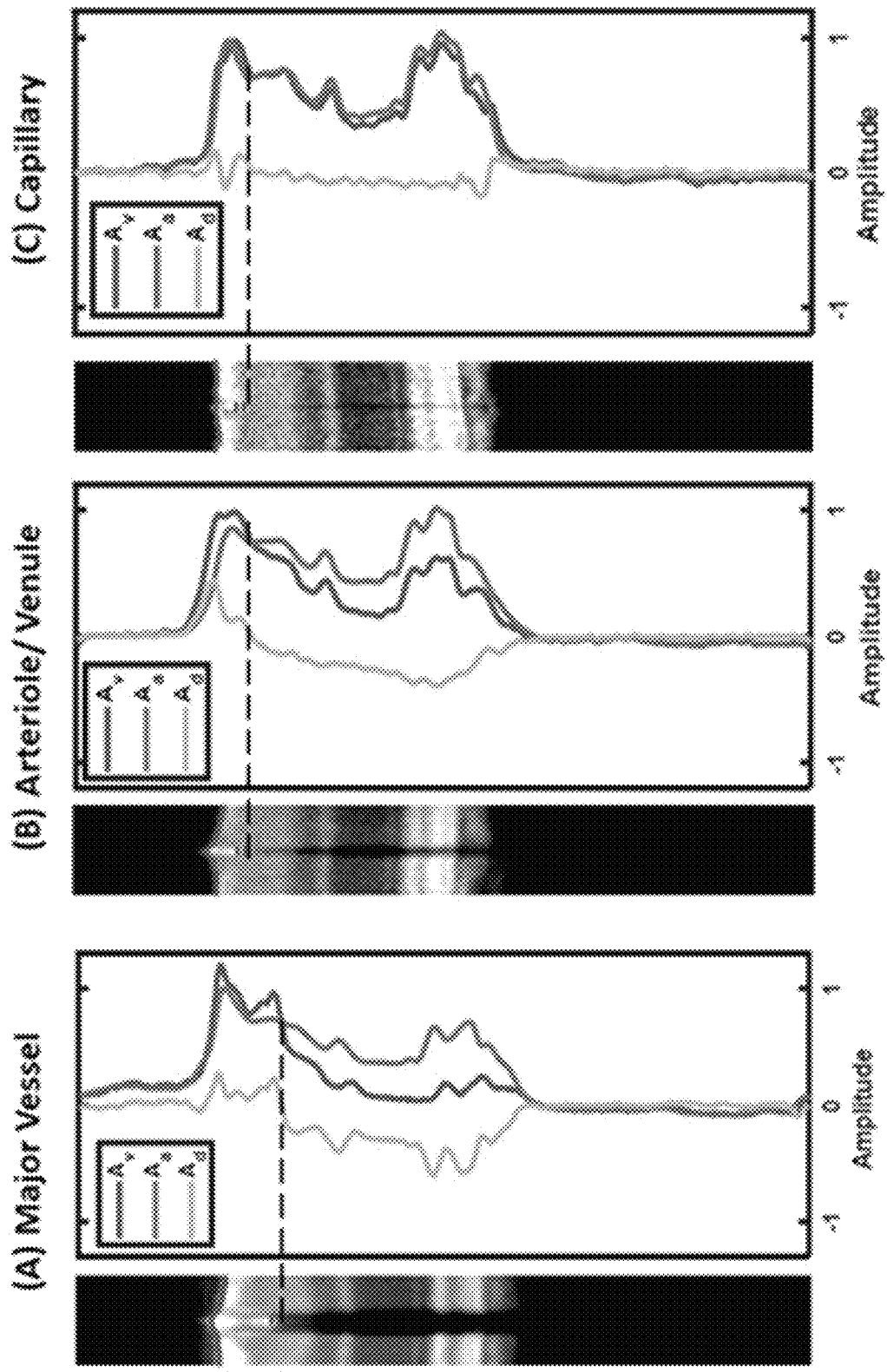
FIGS. 21A, 21B, and 21C illustrate posterior border detection at vessels with different diameters. $A_v$: vessel reflectance axial profile. $A_a$: averaged reflectance axial profile of the entire B-scan. $A_d$: difference of $A_v$ and $A_a$. The vessel posterior border was determined by the zero-crossing depth of the difference profile $A_d$, with the anterior border determined by the first suprathreshold voxel in the axial profile of the averaged capillary angiogram.

The merged angiographic and structural B-scans were then flattened to the ILM boundaries (red line in FIG. 6C) for further processing. Since the reconstructed B-scans were resampled along the capillary segment and averaged, the signal from other capillaries and noise were largely suppressed while only the signal from the specific capillary segment of interest was enhanced. The anterior border of the capillary segment was determined by the first suprathreshold voxel in the averaged capillary angiogram axial profile. Usually, vascular voxels have stronger reflectance and larger decorrelation values (due to the scattering of red blood cells) than neighboring tissues, whereas the voxels underneath vascular pixels have much lower reflectance than neighboring tissues due to severe absorption of hemoglobin in the visible light range. The posterior border (black dashed line in FIG. 6D) of the capillary segment was obtained by finding the zero-crossing position in the reflectance difference axial profile ($A_d$) of the averaged capillary reflectance axial profile ($A_c$) and the averaged reflectance axial profile for the entire B-scan ($A_a$) (FIG. 6D). In summary, the posterior segment identification process, the detailed steps of which appear in FIG. 20, was accomplished by comparing the structural and angiographic axial profiles in capillaries with their neighboring tissues. This method was found to work consistently for vessels of different diameters (see FIGS. 21A-21C).

8.4.5 Spectroscopic Fitting.

The spatial- and depth-resolved optical density OD ($z$, $\lambda$) in the capillary (blue line in FIG. 6E) is defined as the logarithm of the ratio for reflected intensity spectrum I ($z$, $\lambda$) to the source spectrum $I_0$ ($\lambda$). It stands for the reflectivity of the tissue, and is determined by extinction coefficients based on a modified Beer's law as shown in Equation (2) (also described above in Section 5):

$$OD(z, \lambda) = \ln\left(\frac{I(z, \lambda)}{I_0(\lambda)}\right) = -2(z - z_0)[C_{HbO_2}\varepsilon_{HbO_2}(\lambda) + C_{Hb}\varepsilon_{Hb}(\lambda)] - \alpha\ln(\lambda) + \ln(AR_0) \quad (2)$$

Here, $z_0$ and $z$ are the depth of anterior and posterior voxels respectively, and $z-z_0$ is the accumulated absorption length for the vessels. The scattering spectrum of the vessel wall $r(\lambda)$ was modeled as a power law $A \cdot \lambda^{-\alpha}$ under the first-order Born approximation. The scattering spectrum at the reference arm $R_0$ was considered as a wavelength-independent constant. The subscripts $HbO_2$ and Hb indicate the contribution from oxygenated and deoxygenated hemoglobin respectively, with their extinction coefficients ε referring to literature values and concentrations C being calculated by fitting, in order to find the oxygen saturation $sO_2 = C_{HbO_2}/(C_{HbO_2} + C_{Hb})$.

Optical density OD ($z$, $\lambda$) was extracted by a short time Fourier transform (STFT) spectroscopic analysis of the interference fringes (see FIG. 6E). A Gaussian window with a full-width at half-maximum of approximately 9 nm and an interval distance around 3 nm were applied, resulting in 21 split spectra bands in total. Only those bands within the contrast region from 527 nm to 582 nm were selected for linear regression fitting for the $sO_2$.

8.4.6 Capillary Bed Morphology.

The SVC capillary perfusion distance, which was defined as the shortest distance between a capillary segment to a major vessel through the vascular network (see FIGS. 11A-11D), was quantified by using the weighted shortest path problem model. Specifically, the identified capillary segments were assigned as nodes in the model, and the identified bifurcation points were used to construct a connection graph for their capillary segments. The weight of each connection channel $P_{ij}$ was defined as the mean capillary lengths for the $i^{th}$ and $j^{th}$ capillary segments. After obtaining the perfusion distance, node lists of the shortest pathways were also recorded. It should be noted that the capillary perfusion distance for some capillary segments (marked white in FIG. 11B) could not be obtained due to the limited field of view.

By establishing the shortest pathways for all capillary segments to reach a major vessel, we could determine the primary connections along the network. The parent and children branch segments in bifurcations could be determined by comparing their perfusion distances. The upstream and downstream segments for each capillary segment were also determined by the recorded node lists in the shortest pathways, revealing the flow directions of each capillary segment (see FIGS. 22A-22B). After that, the pixel-wised capillary perfusion distance maps were generated by gradually increasing the distance along the flow direction (see FIG. 11B).

Figures 22A, 22B:
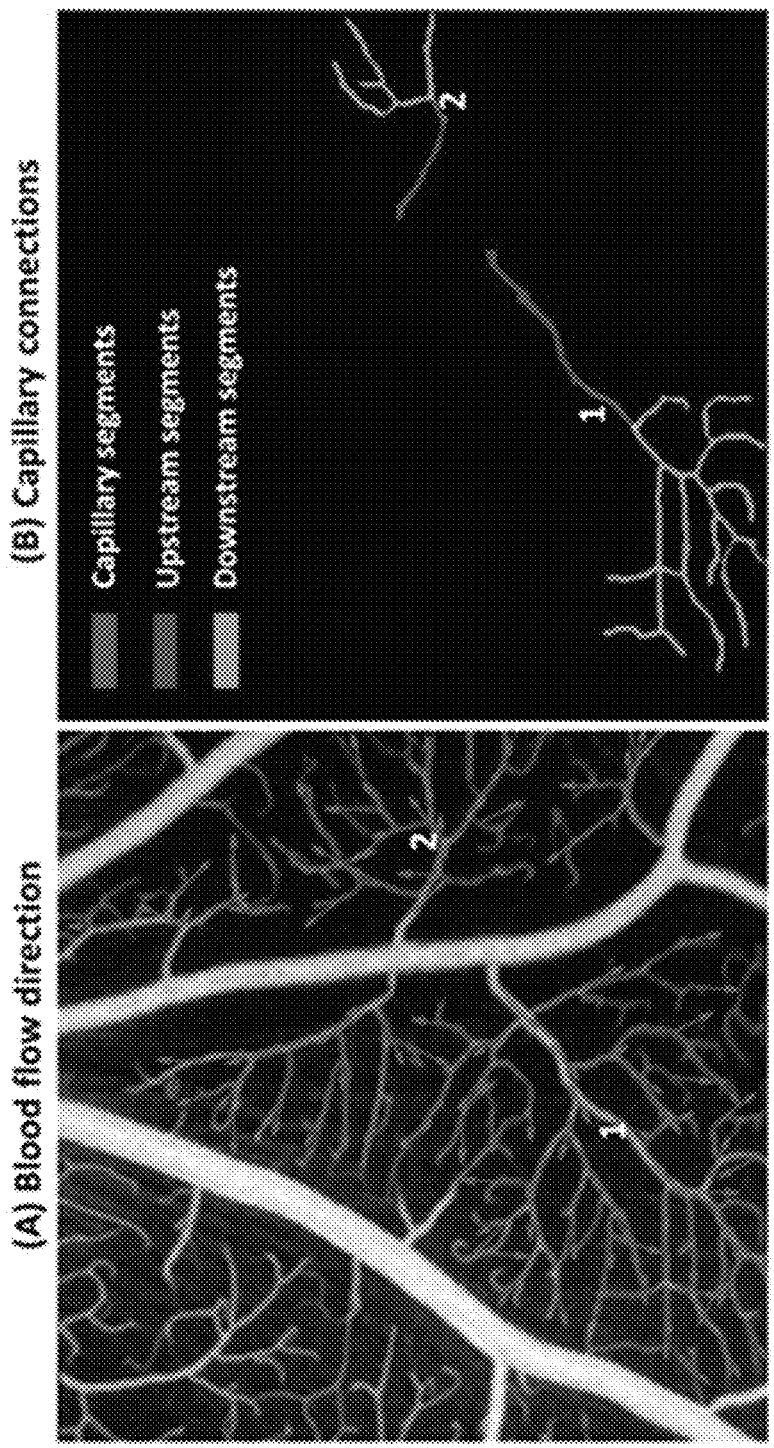
FIG. 22A illustrates blood flow direction in SVP arterial capillaries.
FIG. 22B illustrates examples of capillary connections for capillaries #1 and #2 (labeled in FIG. 22A) revealed during the capillary morphology analysis. Capillary #1 is identified as a first order capillary as it has 22 downstream segments. Capillary #2 is identified as third order capillary as it has 6 downstream segments.

SVC capillary order was further quantified for each capillary segment by counting downstream segments (see FIGS. 22A-22B). As shown in FIG. 11C, the capillary segments were determined as first order (count larger than 20, magenta, which may represent arterioles), second order (count between 19 and 8, yellow), third order (count between 7 and 3, cyan), and fourth order (count between 2 and 1, green) capillary segments. The capillary segments without a downstream capillary segment were identified as fifth order capillary segments (count 0, blue).

8.4.7 Calculation of Retinal Oxygen Pressure Profile from Capillary $sO_2$.

The oxygen demand of retinal tissue is satisfied by the oxygen diffusion from four capillary plexuses, i.e. the SVP, the ICP, the DCP and the choriocapillaris (CC), where the oxygen pressure ($PO_2$) can be calculated from the $sO_2$ values through the oxy-hemoglobin dissociation curve (see FIGS. 23A-23C). As the choroid is a highly vascularized tissue, the $PO_2$ in the choriocapillaris, is assumed to be similar to that in retinal arteries and is obtained from the averaged $sO_2$ in the retinal arteries. Since the retina consists of layers that differ in axial direction, the diffusion can be simplified to a one-dimensional process and described using the second order Fick's law as below, $$Q_i = Dk\frac{d^2 P_i}{dx^2} \quad (3)$$

$$P_i(x) = \frac{Q_i}{2Dk}x^2 + \alpha_i x + \beta_i$$

where Q is oxygen consumption in the layer, D is oxygen diffusivity [$1.97 \times 10^{-5}$ cm$^2$/s], k is to oxygen solubility coefficients [2.4 mL $O_2$/(mL retina·mmHg)], with x [μm] the depth of retina and P(x) the $PO_2$ at that depth. The subscript i indicates the specific slab. Based on the relative depth of four capillary plexuses to these two layers, we could model the retina into six slabs (see FIG. 23B), which are the nerve fiber layer and ganglion cell layer (slab 1), the inner plexiform layer (slab 2), the inner nuclear layer and outer plexiform layer (slab 3), the outer nuclear layer (slab 4), the photoreceptor inner segments (slab 5), and the photoreceptor outer segments and retinal pigment epithelium (slab 6). According to a previous study, the majority of oxygen consumption is in the inner plexiform layer for the inner retina and in the photoreceptor inner segments for the outer retina. Thus, the $Q_1$, $Q_3$, $Q_4$, and $Q_6$ are considered negligible and set to 0 for slabs 1, 3, 4, and 6. By solving the diffusion equation we can model the $PO_2$ profile at each slab (Eq. (3)). By applying the boundary conditions at the four capillaries plexuses and other interface of slabs, the $\alpha_1$-$\alpha_6$, and $\beta_1$-$\beta_6$ are obtained to calculate the $PO_2$ along the depth of retina.

9. Example Optical Coherence Tomography Angiography Image Processing System

Figure 9:
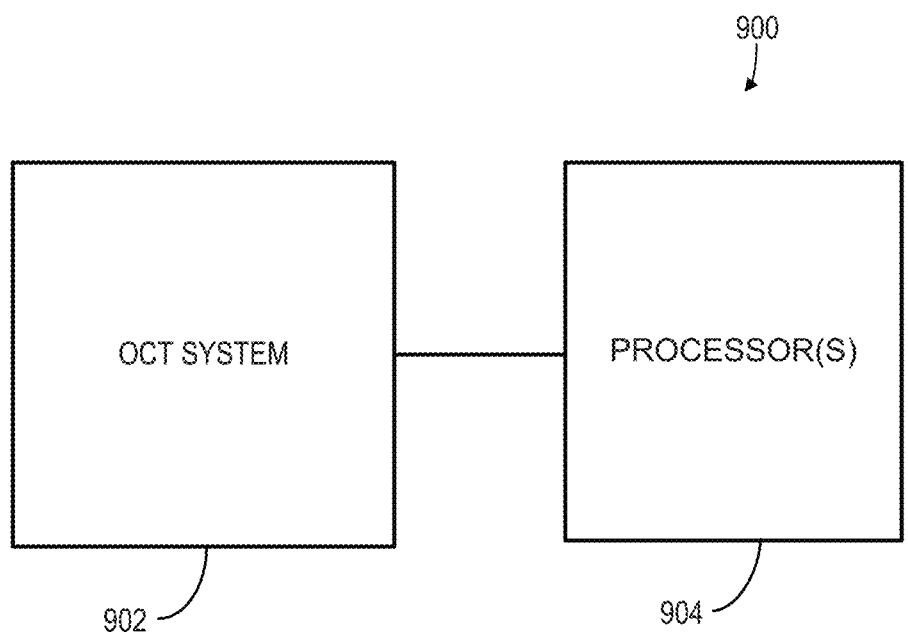
FIG. 9 schematically shows an example system for retinal capillary oximetry using OCT, in accordance with various embodiments.

FIG. 9 schematically shows an example system 900 for OCT image processing in accordance with various embodiments. System 900 comprises an OCT system 902 configured to acquire an OCT image comprising OCT interferograms and one or more processors or computing systems 904 that are configured to implement the various processing routines described herein. OCT system 900 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the method 200 depicted in FIG. 2 and described above, can be implemented as a computer application, computer service, computer API, computer library, and/or other computer program product.

Figure 10:
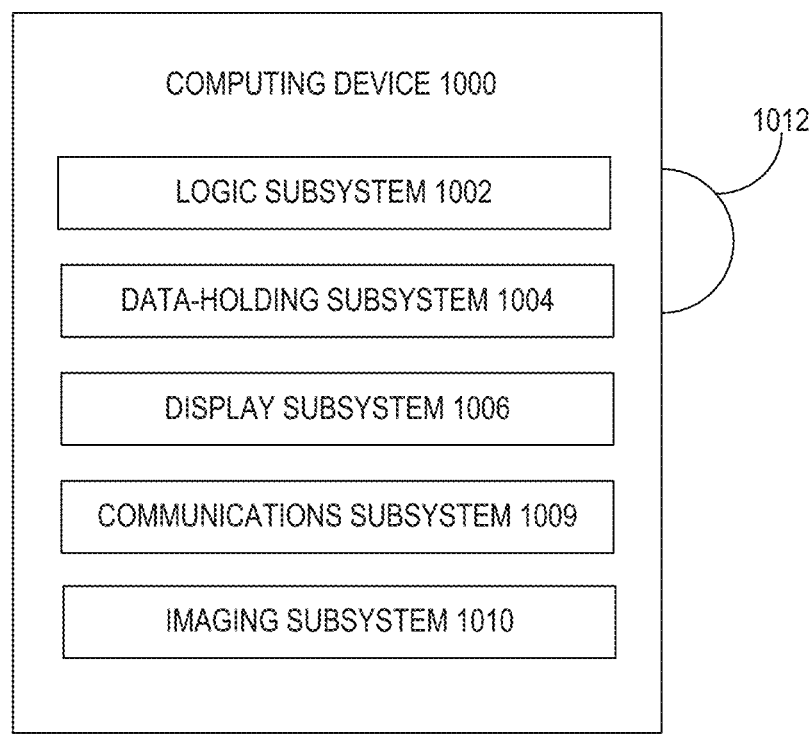
FIG. 10 schematically shows an example of a computing system in accordance with the disclosure.

FIG. 10 schematically shows a non-limiting computing device 1000 that can perform one or more of the above described methods and processes. For example, computing device 1000 can represent a processor included in system 900 described above, and can be operatively coupled to, in communication with, or included in an OCT system or OCT image acquisition apparatus. Computing device 1000 is shown in simplified form. It is to be understood that virtually any computer architecture can be used without departing from the scope of this disclosure. In different embodiments, computing device 1000 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1000 includes a logic subsystem 1002 and a data-holding subsystem 1004. Computing device 1000 can optionally include a display subsystem 1006, a communication subsystem 1008, an imaging subsystem 1010, and/or other components not shown in FIG. 10. Computing device 1000 can also optionally include user input devices such as manually actuated buttons, switches, keyboards, mice, game controllers, cameras, microphones, and/or touch screens, for example.

Logic subsystem 1002 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1004 can include one or more physical, non-transitory, devices configured to hold data and/or instructions executable by the logic subsystem to implement the herein described methods and processes. When such methods and processes are implemented, the state of data-holding subsystem 1004 can be transformed (e.g., to hold different data).

Data-holding subsystem 1004 can include removable media and/or built-in devices. Data-holding subsystem 1004 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1004 can include devices with one or more of the following characteristics: volatile, nonvolatile, dynamic, static, read/write, read-only, random access, sequential access, location addressable, file addressable, and content addressable. In some embodiments, logic subsystem 1002 and data-holding subsystem 1004 can be integrated into one or more common devices, such as an application specific integrated circuit or a system on a chip.

FIG. 10 also shows an aspect of the data-holding subsystem in the form of removable computer-readable storage media 1012, which can be used to store and/or transfer data and/or instructions executable to implement the herein described methods and processes. Removable computer-readable storage media 1012 can take the form of CDs, DVDs, HD-DVDs, Blu-Ray Discs, EEPROMs, flash memory cards, USB storage devices, and/or floppy disks, among others.

When included, display subsystem 1006 can be used to present a visual representation of data held by data-holding subsystem 1004. As the herein described methods and processes change the data held by the data-holding subsystem, and thus transform the state of the data-holding subsystem, the state of display subsystem 1006 can likewise be transformed to visually represent changes in the underlying data. Display subsystem 1006 can include one or more display devices utilizing virtually any type of technology. Such display devices can be combined with logic subsystem 1002 and/or data-holding subsystem 1004 in a shared enclosure, or such display devices can be peripheral display devices.

When included, communication subsystem 1008 can be configured to communicatively couple computing device 1000 with one or more other computing devices. Communication subsystem 1008 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1000 to send and/or receive messages to and/or from other devices via a network such as the Internet.

When included, imaging subsystem 1010 can be used acquire and/or process any suitable image data from various sensors or imaging devices in communication with computing device 1000. For example, imaging subsystem 1010 can be configured to acquire OCT image data, e.g., interferograms, as part of an OCT system, e.g., OCT system 902 described above. Imaging subsystem 1010 can be combined with logic subsystem 1002 and/or data-holding subsystem 1004 in a shared enclosure, or such imaging subsystems can comprise periphery imaging devices. Data received from the imaging subsystem can be held by data-holding subsystem 1004 and/or removable computer-readable storage media 1012, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A system for quantifying oxygen saturation in a retina, the system comprising:
    an optical coherence tomography (OCT) system configured to acquire a structural OCT dataset of the retina based on scans of the retina with visible light;
    a logic subsystem; and
    a data holding subsystem comprising machine-readable instructions stored thereon that are executable by the logic subsystem to:
        obtain an OCT angiography dataset based on the structural OCT dataset;
        perform capillary segmentation on the OCT angiography dataset to obtain capillary segments, wherein to perform the capillary segmentation includes to:
            vesselness filter angiogram data of the OCT angiography dataset to enhance the angiogram data;
            threshold the enhanced angiogram data to obtain a vessel binary mask;
            skeletonize the vessel binary mask to provide a skeleton;
            apply a neighbor-counting filter to identify bifurcation and overlay points in the skeleton; and
            exclude the bifurcation and the overlay points to obtain the capillary segments;
        resample and register B-scans of the OCT angiography dataset that correspond to the capillary segments to obtain registered angiographic B-scans; and
        determine an oxygen saturation in a first capillary segment of the capillary segments based on the registered angiographic B-scans.

2. The system of claim 1, wherein the instructions are further executable by the logic subsystem to average the registered angiographic B-scans associated with the first capillary segment to obtain an averaged angiographic B-scan for the first capillary segment, wherein the oxygen saturation in the first capillary segment is determined based on the registered angiographic B-scans includes determining the oxygen saturation in the first capillary segment based on the averaged angiographic B-scan.

3. The system of claim 2, wherein the instructions are further executable by the logic subsystem to determine an anterior border and a posterior border of the respective capillary segments, wherein the oxygen saturation is further determined based on the anterior border and the posterior border of the one or more capillary segments.

4. The system of claim 3, wherein:
    the anterior border is determined by comparing flow values of the averaged angiographic B-scan to a threshold value; and
    the posterior border is determined by finding a zero-crossing position in a difference axial profile ($A_d$) of an averaged capillary A-line profile ($A_c$) associated with the first capillary segment and an averaged A-line profile ($A_a$) of the averaged angiographic B-scan as a whole.

5. The system of claim 1, wherein the capillary segmentation is performed on a two-dimensional (2-D) en face projection of the OCT angiography dataset.

6. The system of claim 1, wherein the capillary segmentation is performed in three dimensions on the OCT angiography dataset.

7. The system of claim 1, wherein the visible light includes light with wavelengths within a range from 496 nanometers (nm) to 630 nm.

8. The system of claim 1, wherein the oxygen saturation in the first capillary segment is determined according to:

$$OD(z, \lambda) =$$

-continued $$\ln\left(\frac{I(z,\lambda)}{I_0(\lambda)}\right) = -2(z-z_0)[C_{HbO_2}\varepsilon_{HbO_2}(\lambda) + C_{Hb}\varepsilon_{Hb}(\lambda)] - \alpha\ln(\lambda) + \ln(AR_0)$$

wherein $z_0$ is a depth of an anterior voxel of the first capillary segment, z is a depth of a posterior voxel of the first capillary segment, $\lambda$ is a light wavelength used to obtain the structural OCT dataset, $R_0$ is a scattering spectrum at a reference arm, $C_{HbO2}$ is a concentration of oxygenated hemoglobin, $C_{Hb}$ is a concentration of deoxygenated hemoglobin, $\varepsilon_{HbO2}$ is an extinction coefficient of oxygenated hemoglobin, and $\varepsilon_{Hb}$ is an extinction coefficient of deoxygenated hemoglobin; and $$sO_2 = C_{HbO2}/(C_{HbO2}+C_{Hb});$$

wherein $sO_2$ is the oxygen saturation.

9. The system of claim 1, wherein the instructions are further executable by the logic subsystem to determine a capillary perfusion distance for one or more of the capillary segments based on a shortest path distance to another capillary segment that is directly branched from a vessel.

10. The system of claim 1, wherein the instructions are further executable by the logic subsystem to determine a tissue oxygen pressure based on the determined oxygen saturation of the first capillary segment.

11. The system of claim 1, wherein the instructions are further executable by the logic subsystem to:
determine a capillary perfusion distance for one or more of the capillary segments based on a shortest path distance to another capillary segment that is directly branched from a vessel.

12. The system of claim 1, wherein the instructions are further executable by the logic subsystem to:
determine a tissue oxygen pressure based on the determined oxygen saturation of the capillary segment.

13. The system of claim 1, wherein the skeletonizing uses a thinning algorithm to delineate a vascular centerline and collapse vascular caliber information.

14. The system of claim 1, wherein the neighbor-counting filter considers a number of neighboring vascular pixels.

15. A system for quantifying oxygen saturation in a retina, the system comprising:
an optical coherence tomography (OCT) system configured to acquire a structural OCT dataset of the retina based on scans of the retina with visible light;
a logic subsystem; and
a data holding subsystem comprising machine-readable instructions stored thereon that are executable by the logic subsystem to:
obtain an OCT angiography dataset based on the structural OCT dataset;
perform capillary segmentation on the OCT angiography dataset to obtain capillary segments;
determine an anterior border and a posterior border of the respective capillary segments, wherein to determine the anterior border and the posterior border includes to:
resample and register B-scans of the OCT angiography dataset that correspond to the capillary segments to obtain merged angiographic B-scans; and
flatten the merged angiographic B-scans to an inner limiting membrane boundary to obtain flattened angiographic B-scans;
to determine the anterior border includes to detect a first suprathreshold voxel in an angiogram axial profile of the capillary segments based on the flattened angiographic B-scans; and
to determine the posterior border includes to average axial profiles in the capillary segment and in the flattened angiographic B-scans to obtain a reflectance difference axial profile, and determine a first zero-crossing voxel in the reflectance difference axial profile; and
determine an oxygen saturation in a capillary segment of the capillary segments based on the merged registered angiographic B-scans and the anterior border and the posterior border of the capillary segment.

16. The system of claim 15, wherein the merged angiographic B-scans comprise an averaged angiographic B-scan and oxygen saturation in the capillary segment is determined based on the averaged angiographic B-scan.

17. The system of claim 15, wherein:
the anterior border is determined by comparing flow values of the averaged angiographic B-scan to a threshold value; and
the posterior border is determined by finding a zero-crossing position in a difference axial profile ($A_d$) of an averaged capillary A-line profile ($A_c$) associated with the first capillary segment and an averaged A-line profile ($A_a$) of the averaged angiographic B-scan as a whole.

18. A system for quantifying oxygen saturation in a retina, the system comprising:
an optical coherence tomography (OCT) system configured to acquire a structural OCT dataset of the retina based on scans of the retina with visible light;
a logic subsystem; and
a data holding subsystem comprising machine-readable instructions stored thereon that are executable by the logic subsystem to:
obtain an OCT angiography dataset based on the structural OCT dataset;
perform capillary segmentation on the OCT angiography dataset to obtain capillary segments;
determine an anterior voxel and a posterior voxel of a capillary segment of the capillary segments, wherein to determine the anterior voxel and the posterior voxel includes to:
resample and register B-scans of the OCT angiography dataset that correspond to the capillary segments to obtain registered merged angiographic B-scans; and
flatten the merged angiographic B-scans to an inner limiting membrane boundary to obtain flattened angiographic B-scans;
to determine the anterior voxel includes to detect a first suprathreshold voxel in an angiogram axial profile of the capillary segment based on the flattened angiographic B-scans; and
to determine the posterior voxel includes to average axial profiles in the capillary segment and in the flattened angiographic B-scans to obtain a reflectance difference axial profile, and determine a first zero-crossing voxel in the reflectance difference axial profile; and
determine an oxygen saturation in the capillary segment based on the registered angiographic B-scans, wherein the oxygen saturation in the capillary segment is determined according to:

$$OD(z, \lambda) = \ln\left(\frac{I(z, \lambda)}{I_0(\lambda)}\right) = -2(z-z_0)[C_{HbO_2}\varepsilon_{HbO_2}(\lambda) + C_{Hb}\varepsilon_{Hb}(\lambda)] - \alpha\ln(\lambda) + \ln(AR_0)$$

wherein $z_0$ is a depth of the anterior voxel of the capillary segment, z is a depth of the posterior voxel of the capillary segment, $\lambda$ is a light wavelength used to obtain the structural OCT dataset, $R_0$ is a scattering spectrum at a reference arm, $C_{HbO2}$ is a concentration of oxygenated hemoglobin, $C_{Hb}$ is a concentration of deoxygenated hemoglobin, $\varepsilon_{HbO2}$ is an extinction coefficient of oxygenated hemoglobin, and $\varepsilon_{Hb}$ is an extinction coefficient of deoxygenated hemoglobin; and $sO_2 = C_{HbO2}(C_{HbO2} + C_{Hb})$;

wherein $sO_2$ is the oxygen saturation.

19. The system of claim 18, wherein the capillary segmentation is performed on a two-dimensional (2-D) en face projection of the OCT angiography dataset.

\* \* \* \* \*